US008372863B2

(12) United States Patent
Clements et al.

(10) Patent No.: US 8,372,863 B2
(45) Date of Patent: Feb. 12, 2013

(54) TETRAHYDRO-1H-PYRROLO FUSED PYRIDONES

(75) Inventors: Matthew J. Clements, Watchung, NJ (US); Vincent J. Colandrea, North Brunswick, NJ (US); John S. Debenham, Scotch Plains, NJ (US); Jeffrey J. Hale, Westfield, NJ (US); Christina B. Madsen-Duggan, Scotch-Plains, NJ (US); Thomas F. Walsh, Old Bridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 129 days.

(21) Appl. No.: 12/919,199

(22) PCT Filed: Feb. 11, 2009

(86) PCT No.: PCT/US2009/033727
§ 371 (c)(1),
(2), (4) Date: Aug. 24, 2010

(87) PCT Pub. No.: WO2009/108499
PCT Pub. Date: Sep. 3, 2009

(65) Prior Publication Data
US 2011/0009406 A1 Jan. 13, 2011

Related U.S. Application Data

(60) Provisional application No. 61/066,978, filed on Feb. 25, 2008.

(51) Int. Cl.
*A61K 31/44* (2006.01)
*C07D 221/02* (2006.01)
(52) U.S. Cl. ........................................ 514/300; 546/112
(58) Field of Classification Search .................. 514/300; 546/112
See application file for complete search history.

(56) References Cited

U.S. PATENT DOCUMENTS
7,799,782 B2 * 9/2010 Munson et al. ............ 514/234.5

FOREIGN PATENT DOCUMENTS
WO WO2007/136990 A2 11/2007
WO WO2008014307 * 1/2008

OTHER PUBLICATIONS

McDonough Michael A., et al., "Cellular Oxygen Sensing: Crystal Structure of Hypoxia-inducible Factor Prolyl Hydroxylase (PHD2)", PNAS, 2006, vol. 103(26) pp. 9814-9819.

* cited by examiner

*Primary Examiner* — Rei-tsang Shiao
(74) *Attorney, Agent, or Firm* — Patricia A. Shatynski; Valerie J. Camara

(57) ABSTRACT

The present invention relates to tetrahydro-1H-pyrrolo fused pyridone compounds useful as HIF prolyl hydroxylase inhibitors to treat anemia and like conditions.

14 Claims, No Drawings

TETRAHYDRO-1H-PYRROLO FUSED PYRIDONES

CROSS REFERENCE TO RELATED APPLICATIONS

This application is a U.S. National Phase application under 35 U.S.C. §371 of PCT Application No. PCT/US2009/033727, filed Feb. 11, 2009 which claims priority under 35 U.S.C. §119(e) from U.S. Provisional Application Ser. No. 61/066,978, filed Feb. 25, 2008.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-αhydroxylation reaction is less efficient and HIP-α is available to dimerize with HIF-β̃. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

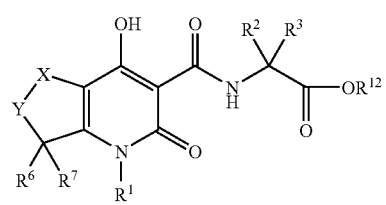

wherein
one of X, or Y, is $NR^8$ and the other moiety is $—CR^4R^5$;
$R^{12}$ is selected from hydrogen, $C_{1-6}$ alkyl, optionally substituted with a hydroxy, $—SH$, $—NH_2$ or $—CO_2H$, and $C_{3-6}$ cycloalkyl optionally substituted with a hydroxy, $—SH$, $—NH_2$ or $—CO_2H$;
n is 1, or 2;
$R^1$ is selected from
— $C_{1-10}$ alkyl,
— $C_{2-10}$ alkenyl,
— $C_{5-10}$ cycloalkenyl,
— $C_{2-10}$ alkynyl,
— $C_{0-10}$ alkylaryl,
— $C_{0-10}$ alkylheterocyclyl;
— $C_{0-10}$ alkyl-$C_{0-10}$cycloalkyl,
— $C_{0-10}$ alkyl$C_{3-10}$heterocycloalkyl, and
perfluoro$C_{1-6}$alkyl;
wherein in $R^1$ said alkyl, alkenyl, alkynyl, cycloalkenyl, aryl, heterocycloalkyl, heterocyclyl, and cycloalkyl are each optionally substituted with one or more $R^9$ substituents;
$R^2$ and $R^3$ are independently selected from hydrogen, phenyl, heterocyclyl, and —$C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl, $C_{1-10}$ alkyl, and —$OC_{1-10}$ alkyl;

$R^8$ is selected from —$C_1$-$C_{10}$ alkyl, —$C_{2-10}$ alkenyl, —($C_{0-10}$ alkyl)$C_{3-10}$ cycloalkyl, —($C_{0-10}$ alkyl) $C_{3-10}$ heterocycloalkyl, —($C_{0-10}$ alkyl)aryl, —($C_{0-10}$ alkyl)heterocyclyl, —($C_{0-10}$ alkyl)$C_{5-10}$ cycloalkenyl, $C_{1-6}$ alkoxy, aryloxy, heterocyclyloxy, —$CO_2R^a$, —$CONR^bR^c$, —$R^aC(=N)NR^bR^c$, —$S(O)_2NR^b$, and —$S(O)_nR^d$, wherein said aryl, heterocyclyl, alkoxy, aryloxy, heterocyclyloxy are optionally substituted by one or more substituents $R^{10}$;

$R^4$, $R^5$, $R^6$, and $R^7$ are independently selected from hydrogen, cyano, oxo, —$C_1$-$C_{10}$ alkyl, —$C_{2-10}$ alkenyl, —$C_{3-10}$ cycloalkyl, —($C_{0-10}$ alkyl)aryl, ($C_{0-10}$ alkyl)heterocyclyl, —$C_{5-10}$ cycloalkenyl, —$C_{2-10}$ alkynyl, —$SO_n(C_{1-10}$ alkyl) and —$SO_n$ aryl wherein said alkyl, alkenyl, alkynyl, cycloalkyl, cycloalkenyl, aryl, and heterocyclyl are optionally substituted by one or more substituents $R^9$, and optionally one set of substituents, $R^4$ and $R^5$, or $R^6$ and $R^7$, are linked together to form a ring of 5 to 8 atoms optionally substituted with one or more substituents $R^9$;

where said ring is partially or fully unsaturated having 0, 1 or 2 heteroatoms independently selected from —$NR^6$—, —O— and —$S(O)_n$—;

$R^9$ is selected from halogen, hydroxy, oxo, cyano, aryl, heterocyclyl, —$C_{1-6}$ alkyl, —$C_{1-6}$ alkoxy, aryloxy, heterocyclyloxy, —$CO_2R^a$, —$NR^bR^c$, —$CONR^bR^c$, —$OCO_2R^a$, —$OCONR^bR^c$, —$NR^dCO_2R^a$, —$NR^dCONR^bR^c$, —$SC_{0-6}$ alkyl and —$S(O)_nR^d$, wherein said aryl, heterocyclyl, alkoxy, aryloxy, heterocyclyloxy are optionally substituted by one or more substituents $R^{10}$;

$R^{10}$ is selected from hydroxy, aryl, heterocyclyl, halogen, oxo, —$C_{1-6}$ alkyl, $C_{1-6}$ alkoxy, halogen, $CO_2H$, cyano, $O(C=O)_{0-1}C_{1-6}$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{0-10}$ alkyloxycarbonylamino$C_{0-10}$ alkyl, $C_{0-10}$ alkylcarbonylamino$C_{0-10}$ alkyl, $C_{0-10}$ alkylaminosulfonylamino$C_{0-10}$ alkyl, $C_{0-10}$ alkylsulfonylamino$C_{0-10}$ alkyl, $C_{0-10}$ alkylsulfonyl, $C_{0-10}$ alkylaminosulfonyl, $C_{0-10}$ alkylaminocarbonyl, —(C=O)N($C_{0-6}$ alkyl)$_2$, —S($C_{0-6}$ alkyl), and $NH_2$;

$R^a$ is chosen from hydrogen; —$C_{1-10}$ alkyl, —($C_{1-6}$ alkyl)$C_{3-8}$ cycloalkyl; and —($C_{1-6}$ alkyl)phenyl; and $R^b$, $R^c$, and $R^d$ are each independently chosen from hydrogen, —$C_{1-10}$ alkyl, —$C_{3-10}$ cycloalkyl, aryl, and heterocyclyl, wherein said alkyl, cycloalkyl, aryl and heterocyclyl are optionally substituted by one or more substituents $R^{10}$.

Illustrative but nonlimiting examples of compounds of the invention are the following:

N-({4-hydroxy-2-oxo-6-pent-4-enoyl-1-[4-(trifluoromethyl)benzyl]-2,5,6,7-tetrahydro-1H-pyrrolo[3,4-b]pyridin-3-yl}carbonyl)glycine;

N-{[1-(biphenyl-4-ylmethyl)-4-hydroxy-2-oxo-6-pent-4-enoyl-2,5,6,7-tetrahydro-1H-pyrrolo[3,4-b]pyridin-3-yl]carbonyl}glycine;

N-{[1-(1,3-benzothiazol-2-ylmethyl)-4-hydroxy-2-oxo-6-pent-4-enoyl-2,5,6,7-tetrahydro-1H-pyrrolo[3,4-b]pyridin-3-yl]carbonyl}glycine;

N-{[1-(3-bromobenzyl)-4-hydroxy-2-oxo-6-pent-4-enoyl-2,5,6,7-tetrahydro-1H-pyrrolo[3,4-b]pyridin-3-yl]carbonyl}glycine;

N-{[1-(4-bromobenzyl)-4-hydroxy-7-methyl-2-oxo-6-pent-4-enoyl-2,5,6,7-tetrahydro-1H-pyrrolo[3,4-b]pyridin-3-yl]carbonyl}glycine;

N-{[1-(4-bromobenzyl)-4-hydroxy-5-methyl-2-oxo-6-pent-4-enoyl-2,5,6,7-tetrahydro-1H-pyrrolo[3,4-b]pyridin-3-yl]carbonyl}glycine;

N-({4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate;

N-({6-(3-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({6-acetyl-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-6-(methylsulfonyl)-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-6-(morpholin-4-ylcarbonyl)-2-oxo-1-[4-(trifluoromethyl)benzyl]-2,5,6,7-tetrahydro-1H-pyrrolo[3,4-b]pyridin-3-yl}carbonyl)glycine;

N-({6-[(dimethylamino)sulfonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({6-(cyclopropylcarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-6-(methoxyacetyl)-2-oxo-1 [4-(trifluoromethyl)benzyl]-2,5,6,7-tetrahydro-1H-pyrrolo[3,4-b]pyridin-3-yl}carbonyl)glycine;

N-({6-(2,2-dimethylpropanoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({6-(ethoxycarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(pyrrolidin-1-ylcarbonyl)-1-[4-(trifluoromethyl)benzyl]-2,5,6,7-tetrahydro-1H-pyrrolo[3,4-b]pyridin-3-yl}carbonyl)glycine;

N-({6-(2-chlorobenzoyl)-4-hydroxy-2-oxo-1 [4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(phenylsulfonyl)-1-[4-(trifluoromethyl)benzyl]-2,5,6,7-tetrahydro-1H-pyrrolo[3,4-b]pyridin-3-yl}carbonyl)glycine;

N-({6-(cyclopentylcarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({6-(4-chlorobenzoyl)-4-hydroxy-2-oxo-1 [4-(trifluoromethyl)benzyl]-2,5,6,7-tetrahydro-1H-pyrrolo[3,4-b]pyridin-3-yl}carbonyl)glycine;

N-{[1-(biphenyl-4-ylmethyl)-6-(ethoxycarbonyl)-4-hydroxy-2-oxo-2,5,6,7-tetrahydro-1H-pyrrolo[3,4-b]pyridin-3-yl]carbonyl}glycine;

N-({6-[(1,3-dimethyl-1H-pyrazol-5-yl)carbonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(pyrazolo[1,5-a]pyrimidin-2-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(pyridin-3-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-6-[(6-methylpyridin-3-yl)carbonyl]-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-6-(1-methyl-L-prolyl)-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(5-oxo-L-prolyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,3-thiazol-4-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,3-thiazol-5-ylcarbonyl)-1-[4-(trifluoromethyl)benzyl]-2,5,6,7-tetrahydro-1H-pyrrolo[3,4-b]pyridin-3-yl}carbonyl)glycine;

N-({6-[(1,5-dimethyl-1H-pyrazol-2-ium-3-yl)carbonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine chloride;

N-({4-hydroxy-6-{[(2S)-1-methylpyrrolidinium-2-yl]carbonyl}-2-oxo-1-[4-(trifluoromethyl)benzyl]-2,5,6,7-tetrahydro-1H-pyrrolo[3,4-b]pyridin-3-yl}carbonyl)glycine trifluoroacetate;

N-({4-hydroxy-6-(isoxazol-5-ylcarbonyl)-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,3-thiazol-2-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,2,3-thiadiazol-4-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-6-[(6-methylpyridinium-3-yl)carbonyl]-2-oxo-1-[4-(trifluoromethyl)benzyl]-2,5,6,7-tetrahydro-1H-pyrrolo[3,4-b]pyridin-3-yl}carbonyl)glycine trifluoroacetate;

N-({4-hydroxy-6-(1,3-oxazol-4-ylcarbonyl)-2-oxo-1-[4-(trifluoromethyl)benzyl]-2,5,6,7-tetrahydro-1H-pyrrolo[3,4-b]pyridin-3-yl}carbonyl)glycine;

N-{[1-(biphenyl-4-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-({6-(4-chlorobenzyl)-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate;

N-({6-(3-chlorobenzyl)-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine chloride;

N-({6-ethyl-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate;

N-({6-(3 cyanopyridinium-2-yl)-4-hydroxy-2-oxo-1-[4-(trifluoromethyl)benzyl]-2,5,6,7-tetrahydro-1H-pyrrolo[3,4-b]pyridin-3-yl}carbonyl)glycine trifluoroacetate;

N-{[1-(biphenyl-3-ylmethyl)-4-hydroxy-2-oxo-6-pent-4-enoyl-2,5,6,7-tetrahydro-1H-pyrrolo[3,4-b]pyridin-3-yl]carbonyl}glycine;

N-{[1-(biphenyl-3-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-[(4'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[4-hydroxy-2-oxo-1-(3-pyrimidin-5-ylbenzyl)-6-(1,3-thiazol-4-ylcarbonyl)-2,5,6,7-tetrahydro-1H-pyrrolo[3,4-b]pyridin-3-yl]carbonyl}glycine;

N-{[1-[(2'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(biphenyl-4-ylmethyl)-4-hydroxy-7-methyl-2-oxo-6-pent-4-enoyl-2,5,6,7-tetrahydro-1H-pyrrolo[3,4-b]pyridin-3-yl]carbonyl}glycine;

N-{[1-(biphenyl-2-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-[(3'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[4-hydroxy-2-oxo-1-(3-pyridin-4-ylbenzyl)-6-(1,3-thiazol-3-ium-4-ylcarbonyl)-2,5,6,7-tetrahydro-1H-pyrrolo[3,4-b]pyridin-3-yl]carbonyl}glycine trifluoroacetate;

N-{[4-hydroxy-2-oxo-1-(3-pyridin-3-ylbenzyl)-6-(1,3-thiazol-3-ium-4-ylcarbonyl)-2,5,6,7-tetrahydro-1H-pyrrolo[3,4-b]pyridin-3-yl]carbonyl}glycine trifluoroacetate;

N-{[1-[3-(6-fluoropyridin-3-yl)benzyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-benzyl-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(biphenyl-4-ylmethyl)-4-hydroxy-7-methyl-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(2-cyanobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine; and pharmaceutically acceptable salts and solvates thereof:

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl, "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH—($C_1$-$C_6$ alkyl)NHC(O)—NH($C_1$-$C_6$ alkyl), NHC(O)OC$_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond; or when the term appears at the terminus of a substituent, $C_{0-6}$ alkyl means hydrogen or C1-6 alkyl. Similarly, when an integer defining the presence of a certain number of atoms in a group is equal to zero, it means that the atoms adjacent thereto are connected directly by a bond. For example, in the structure

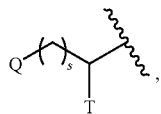

wherein s is an integer equal to zero, 1 or 2, the structure is

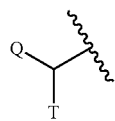

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

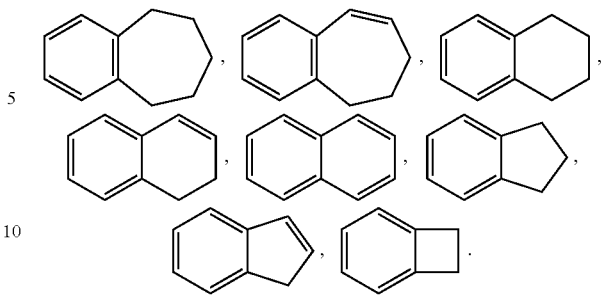

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl(i.e.,

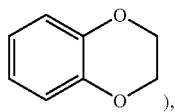

imidazo(2,1-b)(1,3)thiazole, (i.e.,

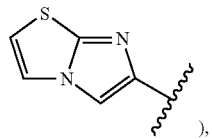 [SMILES: *c1cn2ccsc2n1]

and benzo-1,3-dioxolyl (i.e.,

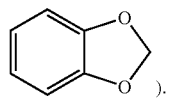

In certain contexts herein,

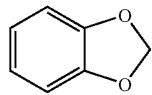

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)$S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)— ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

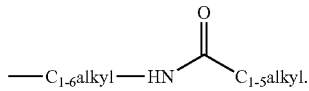

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment of the invention, $R^1$ is selected from $—C_{1-10}$ alkyl, $—C_{0-10}$ alkylaryl, $—C_{0-10}$ alkylheterocyclyl; $—C_{0-10}$ alkyl$C_{3-10}$cycloalkyl, and perfluoro$C_{1-6}$alkyl.

In a subset of this embodiment, $R^1$ is selected from $—C_{0-10}$ alkylaryl, and $—C_{0-10}$ alkylheterocyclyl.

In one embodiment of the invention, the aryl moiety of $R^1$, is selected from phenyl, naphthyl, tetrahydro-naphthyl, indanyl, 2,3-dihydro-1H-indenyl, and biphenyl.

In a subset of this embodiment, the aryl moiety of $R^1$, is selected from phenyl, and biphenyl.

The heterocyclyl moiety in $R^1$, includes, but is not limited to, the following: azabenzimidazolyl, benzoimidazolyl, benzofuryl, benzofurazanyl, benzopyrazolyl, benzotriazolyl, benzothiophenyl, benzothiazolyl, benzothienyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, pyrimidinylphenyl, pyridinylphenyl, and benzo-1,3-dioxolyl.

In a variant of this embodiment, the heterocyclyl moiety in $R^1$ includes azabenzimidazolyl, benzoimidazolyl, benzofuryl, benzopyrazolyl, benzotriazolyl, benzothiophenyl, benzothiazolyl, benzothienyl, benzoxazolyl, carbazolyl, carbolinyl, (uranyl, imidazolyl, indolinyl, indolyl, indolazinyl, indazolyl, isobenzofuryl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridazinyl, pyridinyl, pyrimidyl, pyrrolyl, quinazolinyl, quinolyl, tetrahydropyranyl, tetrazolyl, thiadiazolyl, thiazolyl, thienyl, triazolyl, azetidinyl, piperazinyl, piperidinyl, pyrrolidinyl, morpholinyl, thiomorpholinyl, dihydrobenzoimidazolyl, methylenedioxybenzyl, tetrahydrofuryl, tetrahydrothienyl, tetrahydroquinolinyl, pyrimidinylphenyl, pyridinylphenyl.

In another embodiment, the heterocyclyl moiety of $R^1$ is selected from: pyrimidinylphenyl, pyridinylphenyl, pyridinyl, thiazolyl, oxadiazolyl, benzothiazolyl, oxazolyl, quinolyl, benzothienyl, pyrazolyl, pyrazinyl, and pyridinyl. In a variant of this embodiment, $R^1$ is selected from: pyrimidinylphenyl, pyridinylphenyl, and benzothiazolyl.

In one embodiment of the present invention, $R^1$ is selected from $—C_{1-3}$ alkylaryl, and $—C_{1-3}$ alkylheterocyclyl.

In one embodiment of the invention, $R^{12}$ is selected from hydrogen, and $C_{1-6}$ alkyl, optionally substituted with a hydroxy, $—SH$, $—NH_2$ or $—CO_2H$.

In a variant of this embodiment, $R^{12}$ is hydrogen.

In an embodiment of the present invention, $R^2$ and $R^3$ are each independently selected from hydrogen, and $—C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl, $C_{1-10}$ alkyl, and $—OC_{1-10}$ alkyl.

In a subset of this embodiment, $R^2$ and $R^3$ are each hydrogen.

In one embodiment, $R^4$, $R^5$, $R^6$, and $R^7$ are independently selected from hydrogen, $—C_1$-$C_{10}$ alkyl, $(C_{0-10}$ alkyl)aryl, $(C_{0-10}$ alkyl)heteroaryl, wherein said alkyl, aryl, and heteroaryl are optionally substituted by one or more substituents $R^9$.

In a subset of the above-mentioned embodiment, $R^4$, $R^5$, $R^6$, and $R^7$ are selected from $C_{1-10}$alkyl optionally substituted by one or more substituents $R^9$ and hydrogen.

In one embodiment, $R^8$ is selected from selected from $—C_1$-$C_{10}$ alkyl, $—C_{2-10}$ alkenyl, $—(C_{0-10}$ alkyl)$C_{3-10}$ cycloalkyl, $—(C_{0-10}$ alkyl)$C_{3-10}$ heterocycloalkyl, $—(C_{0-10}$ alkyl)aryl, $—(C_{0-10}$ alkyl)heterocyclyl, $C_{1-6}$ alkoxy, aryloxy, heterocyclyloxy, $—S(O)_2NR^b$, and $—S(O)_nR^d$, wherein said aryl, heterocyclyl, alkoxy, aryloxy, heterocyclyloxy are optionally substituted by one or more substituents $R^{10}$.

In another embodiment, $R^8$ is selected from selected from $—C$ alkyl, $—C_{2-10}$ alkenyl, $—(C_{1-10}$ alkyl)$C_{3-10}$ cycloalkyl, $—(C_{1-10}$ alkyl)$C_{3-10}$ heterocycloalkyl, $—(C_{1-10}$ alkyl)aryl, $—(C_{1-10}$ alkyl)heterocyclyl, $C_{1-6}$ alkoxy, aryloxy, heterocyclyloxy, $—S(O)_2NR^b$, and $—S(O)_nR^d$, wherein said aryl, heterocyclyl, alkoxy, aryloxy, heterocyclyloxy are optionally substituted by one or more substituents $R^{10}$.

Structural representations of compounds having substituents terminating with a methyl group may display the terminal methyl group either using the characters "$CH_3$", e.g. "$—CH_3$" or using a straight line representing the presence of the methyl group, e.g., "$—$", i.e.,

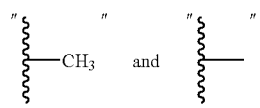

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

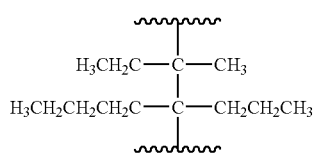

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

ABBREVIATIONS USED IN THE DESCRIPTION
OF THE PREPARATION OF THE COMPOUNDS
OF THE PRESENT INVENTION

| | |
|---|---|
| AcOH | Acetic acid |
| Aq | Aqueous |
| Brine | Saturated aqueous sodium chloride solution |
| $CH_2Cl_2$ | Dichloromethane |
| DMF | N,N-Dimethylformamide |
| Dppf | 1,1"-bis(diphenylphosphino)ferrocene |
| DBU | 1,8-diazabicyclo[5.4.0]undec-7-ene |
| DIEA | N,N-diisopropylethylamine |
| DMAP | 4-N,N-dimethylaminopyridine |
| DMF | N,N-dimethylformamide |
| DMSO | Dimethyl sulfoxide |
| EtOAc | Ethyl acetate |
| Et (et) | Ethyl |
| EtOH | Ethanol |
| $Et_2O$ or ether | Diethyl ether |
| G | Grams |
| h or hr | Hour |
| HCl | Hydrochloric acid |
| HPLC | High-performance liquid chromatography |
| IPA | 2-propanol |
| i-PrOH | Isopropyl alcohol |
| Mg | Milligrams |
| mL | Milliliters |
| Mmol | Millimole |
| MeCN | Acetonitrile |
| MeOH | Methanol |
| Min | Minutes |
| ms or MS | Mass spectrum |
| μL | Microliters |
| NaOEt | Sodium ethoxide |
| NaOMe | Sodium methoxide |
| $Na_2SO_4$ | Sodium sulfate |
| $R_t$ | Retention time |
| Rt or r | Room temperature |
| TFA | Trifluoroacetic acid |
| THF | Tetrahydrofuran |
| μL | Microliters |

Synthesis

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

One embodiment of this invention consists of the substituted N-[(4-hydroxy-2-oxo-2,5,6,7-tetrahydro-1H-pyrrolo[3,4-b]pyridin-3-yl)carbonyl]glycines represented by structural formula Ia shown in Figure 1. The second Another embodiment of this invention consists of the substituted N-[(7-hydroxy-5-oxo-2,3,3a,4,5,7a-hexahydro-1H-pyrrolo[3,2-b]pyridin-6-yl)carbonyl]glycines of formula Ib, also shown in Figure 1.

FIG. 1

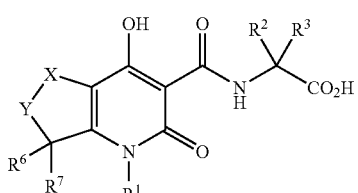

Ia X = CR⁴R⁵, Y = NR⁸
Ib X = NR⁸, Y = CR⁴R⁵

Several strategies based upon synthetic transformations known in the literature of organic synthesis may be employed for the preparation of the title compounds of general formulae Ia and Ib. A synthetic sequence which is presented retrosynthetically is illustrated in reaction Scheme 1, where the substituent PG in structures 1a,b and 2a,b designates an amino protecting group. This synthetic sequence involves the initial preparation of optionally substituted alkyl oxopyrrolidinecarboxylates of general formula 2a and 2b. In the next steps, a pyridone ring is annulated to the b-face of the pyrrolidine ring of 2a or 2b to afford the substituted alkyl oxopyrrolopyridinecarboxylates of general formula 1a and 1b. In the last stage of the synthesis, the ester at the pyridone 3-position of compounds 1a and 1b is converted to the optionally substituted glycineamide sidechain, and the R⁸ substituent is introduced.

One sequence for the synthesis of compounds of general formula Ia is illustrated in reaction Schemes 2-4, and another sequence for the synthesis of compounds of general formula Ib is illustrated in reaction Schemes 5-7 below.

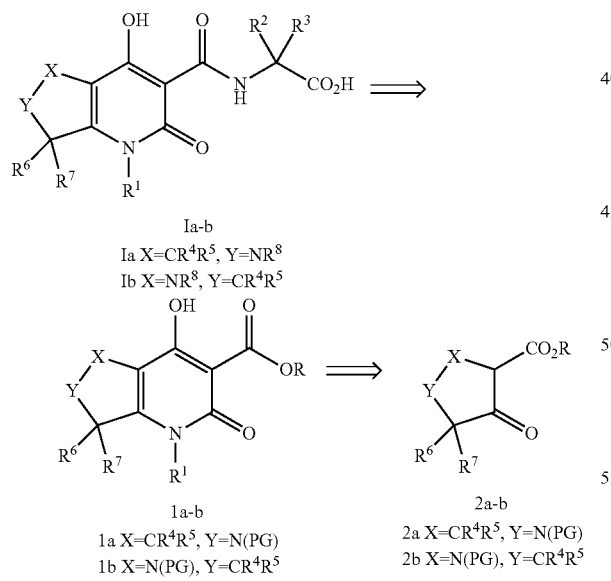

As indicated above, the method for the synthesis of compounds of general formula Ia, representing the first embodiment of the title compounds of this invention, begins with an amino-protected alkyl 4-oxopyrrolidine-3-carboxylate of general formula 2a. In some cases the alkyl 4-oxopyrrolidine-3-carboxylate may be commercially available and subjected to amino group protection to afford compounds of general formula 2a. Alternatively, compounds of general formula 2a (e.g. 7) may be prepared using the sequential Michael addition and Dieckmann condensation methodology published by Moreno-Mañas et al. (Roglans, A.; Marquet, J.; Moreno-Mañas, M. *Syn. Comm.* 1992, 22, 1249-58) and illustrated in reaction Scheme 2. In this synthesis, a substituted alkyl glycinate 3, or salt thereof, is reacted with a substituted acrylate ester of general formula 4 in a solution of aqueous sodium hydroxide. After workup of the reaction mixture and purification, the Michael adduct of general formula 5 is obtained. The secondary amino group of the compound of general formula 5 is next protected so that it will be unreactive during a subsequent acylation reaction of a different amino group.

Numerous protecting groups for amines are known in the art of organic synthesis; however a pentenoylamide (Debenham, J. S.; Madsen, R.; Roberts, C.; Fraser-Reid, B. *J. Amer. Chem. Soc.* 1995, 117, 3302-3) is a particularly useful protecting group because it can be readily removed at a later stage of the synthesis in the presence of a tert-butyl ester (vide infra). Consequently, compounds of general formula 5 are converted to their corresponding pentenoylamides of general formula 6 using the method described by Fraser-Reid et al. The compound of general formula 6 is then subjected to an intramolecular Dieckmann cyclization to afford a protected alkyl 4-oxopyrrolidine-3-carboxylate of general formula 7. This reaction is conducted using a base such as an alkali metal alkoxide in an alcohol as solvent, wherein the alcohol is chosen to correspond to the alkyl groups present in the compounds of general formula 6 in order to avoid forming mixtures of esters in the product of general formula 7. The cyclization reaction is typically conducted at a temperature between room temperature and the reflux temperature of the alcohol and it generally proceeds to completion rapidly, for instance in 0.25 to 4 hours.

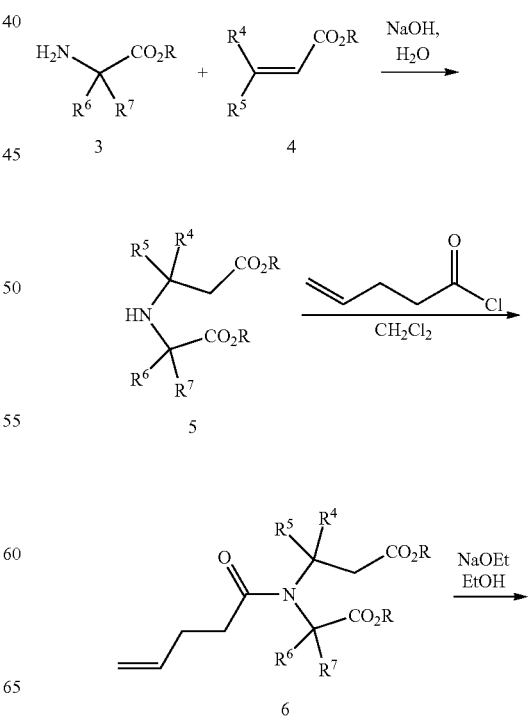

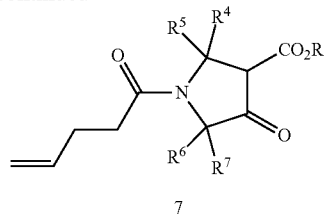

The next steps of the synthesis of the title compounds of general formula Ia are shown in reaction Scheme 3. The protected alkyl 4-oxopyrrolidine-3-carboxylate of general formula 7 is reacted with a primary amine of general formula 8 to provide a vinylogous amide of general formula 9. This reaction is typically conducted in a solvent such as ethanol at elevated temperature, for instance at a temperature between 50° C. and 80° C., and the reaction is usually competed in 1-24 hours. In some instances, formation of the vinylogous amide may be catalyzed by addition of several mole percent of acetic acid to the reaction mixture. Alternatively, if the primary amine of general formula 8 is obtained in the form of a salt such as a hydrochloride salt, then an equivalent of a tertiary amine base such as triethylamine is typically added to the reaction mixture.

Once formation of the vinylogous amide 9 is complete, the reaction mixture is worked up and the product may be either purified chromatographically or used directly in the next step. The compounds of general formula 9 are then acylated with methyl malonyl chloride to afford the substituted alkyl 2,5-dihydro-1H-pyrrole-3-carboxylate derivative of general formula 10. Compounds of general formula 10 are typically isolated from the reaction mixture using a standard workup procedure, then used in the next reaction without further purification.

The next step of the synthesis of the novel compounds of general formula Ia is an intramolecular Dieckmann reaction of a compound of general formula 10 to afford the substituted alkyl 4-hydroxy-2-oxo-2,5,6,7-tetrahydro-1H-pyrrolo[3,4-b]pyridine-3-carboxylate of general formula 11. This cyclization reaction is typically conducted using 1-2 equivalents of an alkali metal alkoxide as the base and the corresponding alcohol as solvent. The alcohol and the alkoxide employed are chosen to correspond to the alkyl substituent on the ester in the compound of general formula 10 to prevent the formation of mixtures of esters. The cyclization reaction is typically conducted at room temperature or slightly above room temperature and the reaction generally proceeds to completion rapidly, for instance in 0.25 to 4 hours.

Scheme 3

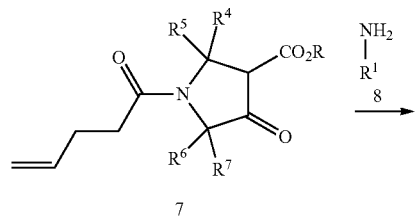

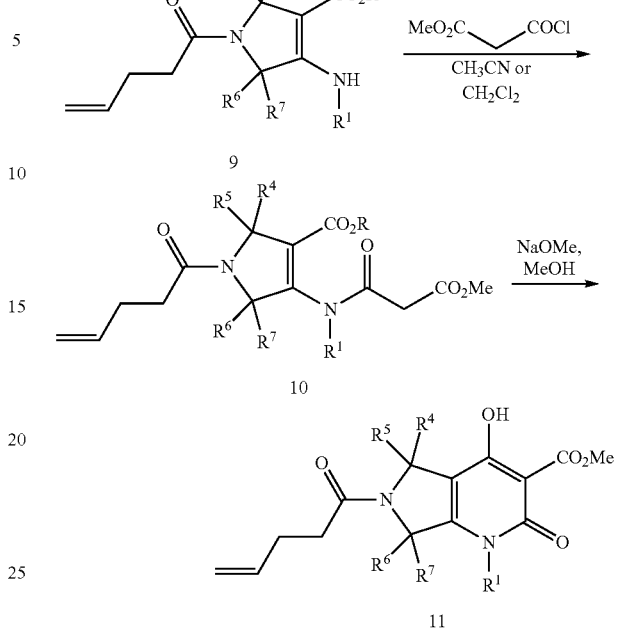

The final steps in the synthesis of the compounds of general formula Ia involve the conversion of the ester group of a compound of general formula 11 to the substituted glycineamide substituent present at the 3-position of the pyridine ring, deprotection of the pyrrolidine N-protecting group and incorporation of the R⁸ substituent as shown in reaction Scheme 4. The first of these transformations may be conducted by first hydrolyzing the 3-position ester in the compound of general formula 11 to the corresponding carboxylic acid and then coupling it with a substituted glycine derivative of general formula 13 using standard amide bond coupling methods. One method for the conversion of 11 to 14 involves heating the ester 11 with the glycine derivative (13) in a suitable solvent which produces the amide 14 in a single step. This latter transformation is typically conducted in a solvent such as n-propanol at temperatures between 80 and 100° C. for periods of 1-5 hours.

Scheme 4

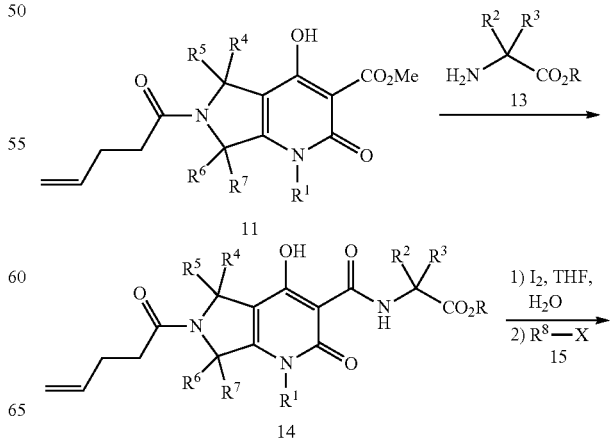

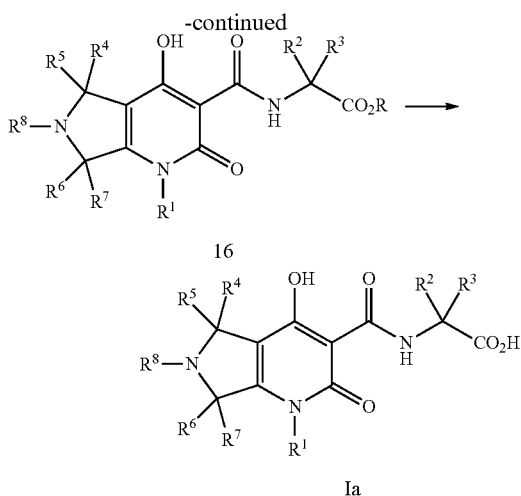

16

Ia

At this point in the synthesis the protecting group on the pyrrolidine ring nitrogen atom is removed. The deprotection is accomplished using iodine in a solution of tetrahydrofuran and water as described by Fraser-Reid et al. and the compound of general formula 16 ($R^8$=H) is produced. If it is desired that the $R^8$ substituent in the title compounds of general formula Ia be a group other than a hydrogen atom, then the $R^8$ substituent is then introduced. Reaction Scheme 4 illustrates the two step process wherein the pentenoylamide protecting group of the compounds of general formula 14 is first removed and the resulting secondary amino group is reacted with a generalized alkylating, acylating, or sulfonylating reagent of general formula 15. In this example, the group X in compounds of general formula 15 indicates a leaving group such as a halide, mesylate, triflate or the like. However it is also within the scope of this invention that the $R^8$ substituent be incorporated into compounds of general formula 16 by other methods know in organic synthesis, for instance using reductive amination reactions with suitable carbonyl compounds, or using the palladium-catalyzed cross coupling reactions of amines described by Buchwald and others (Kienle, M.; Dubbaka, S. R.; Brade, K.; Knochel, P. Eur. J. Org. Chem. 2007, 25, 4166-76).

The final step in the synthesis of the novel compounds of general formula Ia is the conversion of the glycine ester of the intermediate of general formula 6 to the corresponding carboxylic acid. One method to accomplish this, comprises selecting a glycine derivative of general formula 13 wherein the R group is a tert-butyl group. It is then possible to hydrolyze the glycinate of general formula 16 by treatment with an acid such as trifluoroacetic acid in a solvent like dichloromethane to afford a compound of general formula Ia. This reaction is typically conducted at room temperature or a slightly above room temperature and the reaction is conducted for periods of a few hours to overnight. If the substituent R present in the ester of general formula 16 is methyl, ethyl or the like, then a standard hydrolysis reaction under basic conditions converts the ester 16 to the glycineamide derivative of general formula Ia.

One method for the synthesis of compounds of general formula Ib, representing the second embodiment of the title compounds of this invention, begins with an amino-protected alkyl 3-oxoprolinate of general formula 2b. In some cases the alkyl 3-oxoprolinate may be commercially available and subjected to amino group protection to afford compounds of general formula 2b or 17 (reaction Scheme 5). Alternatively, methods for the synthesis of alkyl 3-oxoprolinates appear in the literature of organic synthesis, for instance the method described by Pellegrini et al. (Pellegrini, N.; Schmitt, M.; Guery, S.; Bourguignon, J.-J. Tetrahedron Lett., 2002, 43, 3243-46) or the method of Moreau and Sorensen (Moreau, R. J.; Sorensen, E. J. Tetrahedron 2007, 63, 6446-53).

The protected alkyl 3-oxoprolinates (2b) described in these references may be used in the methods illustrated in reaction Schemes 6 and 7 to prepare the title compounds of general formula Ib particularly when the selected protecting group is a pentenoylamide as shown in the compounds of general formula 17. As discussed above, the pentenoylamide is a useful protecting group because it may be readily removed in the presence of a tert-butyl ester (Debenham, J. S.; Madsen, R.; Roberts, C.; Fraser-Reid, B. J. Amer. Chem. Soc. 1995, 117, 3302-3). Alternatively, when a different protecting group is employed for the synthesis of the compounds of general formula 2b, that protecting group may be removed using appropriate conditions and then converted to the corresponding pentenoylamide as shown in reaction Scheme 5.

Scheme 5

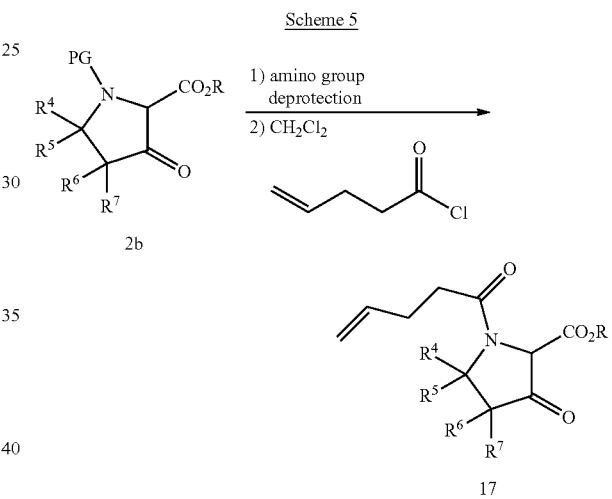

The next steps of the synthesis of the title compounds of general formula Ib are shown in reaction Scheme 6. The pentenoylamide-protected alkyl 3-oxoprolinate of general formula 17 is reacted with a primary amine of general formula 8 to provide a vinylogous amide of general formula 18. This reaction is typically conducted in a solvent such as ethanol at elevated temperature, for instance at a temperature between 50° C. and 80° C., and the reaction is usually competed in 1-24 hours. In some instances, formation of the vinylogous amide may be catalyzed by addition of several mole percent of acetic acid to the reaction mixture. Alternatively, if the primary amine of general formula 8 is obtained in the form of a salt such as a hydrochloride salt, then an equivalent of a tertiary amine base such as triethylamine is typically added to the reaction mixture.

Once formation of the vinylogous amide 18 is complete, the reaction mixture is worked up and the product may be either purified chromatographically or used directly in the next step. The compounds of general formula 18 are then acylated with methyl malonyl chloride to afford the substituted alkyl 3-amino-1-pent-4-enoyl-4,5-dihydro-1H-pyrrole-2-carboxylate derivative of general formula 19. Compounds of general formula 19 are typically isolated from the reaction mixture using a standard workup procedure, then used in the next reaction without further purification.

The next step of the synthesis of the compounds of general formula Ib is an intramolecular Dieckmann reaction of a compound of general formula 19 to afford the substituted alkyl 7-hydroxy-5-oxo-1-pent-4-enoyl-2,3,4,5-tetrahydro-1H-pyrrolo[3,2-b]pyridine-6-carboxylate of general formula 20. This cyclization reaction is typically conducted using 1-2 equivalents of an alkali metal alkoxide as the base and the corresponding alcohol as solvent. The alcohol and the alkoxide employed are again chosen to correspond to the alkyl substituent on the ester in the compound of general formula 19 to prevent the formation of mixtures of esters. The cyclization reaction is typically conducted at room temperature or slightly above room temperature and it generally proceeds to completion rapidly, for instance in 0.25 to 4 hours.

formula 20 to the corresponding carboxylic acid and then coupling it with a substituted glycine derivative of general formula 13 using standard amide bond coupling methods. A useful method for the conversion of 21 to 22 involves heating the ester 21 with the glycine derivative (13) in a suitable solvent which produces the amide 22 in a single step. This latter transformation is typically conducted in a solvent such as n-propanol at temperatures between 80 and 100° C. for periods of 1-5 hours.

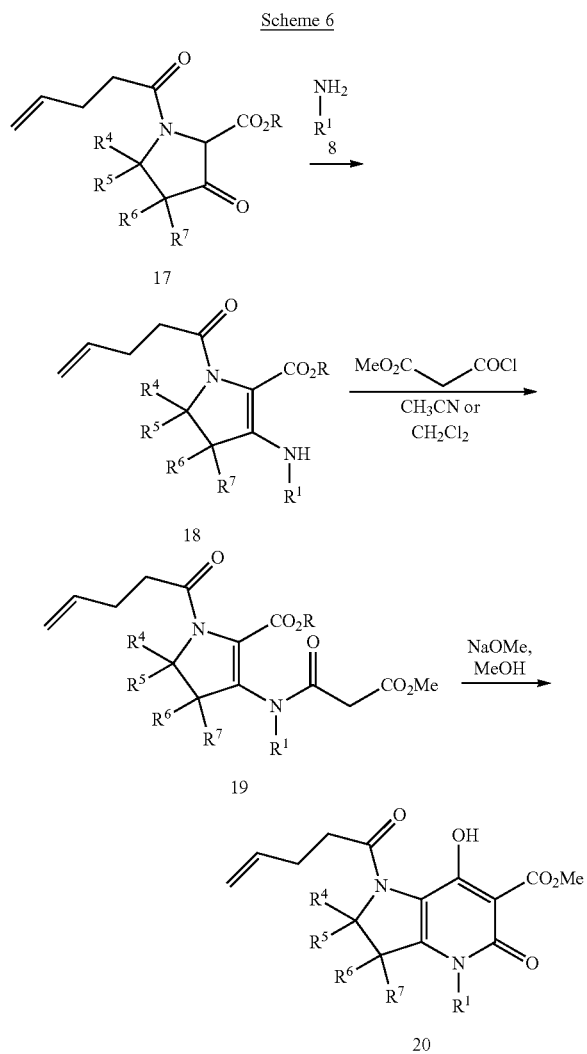

Scheme 6

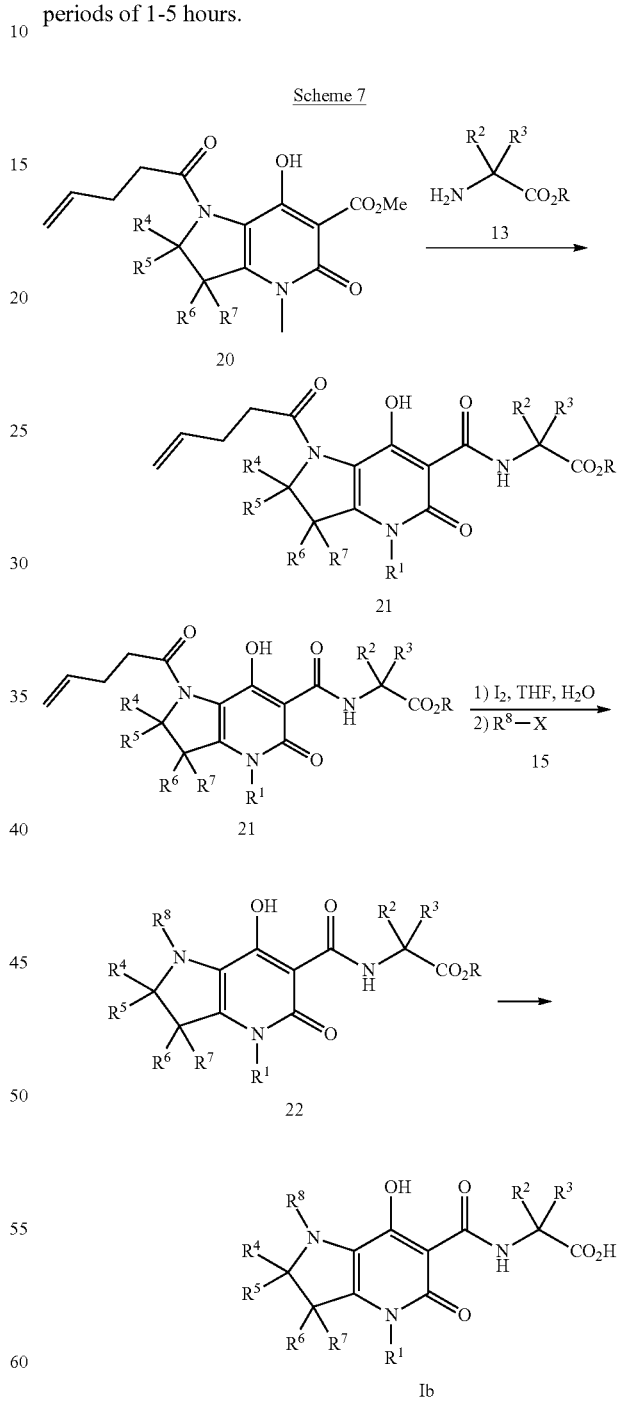

Scheme 7

The final steps in the synthesis of the compounds of general formula Ib involve the conversion of the ester group of a compound of general formula 20 to the substituted glycineamide substituent present at the 3-position of the pyridine ring, deprotection of the pyrrolidine N-protecting group and incorporation of the $R^8$ substituent as shown in reaction Scheme 7. The first of these transformations may be conducted by first hydrolyzing the 3-position ester in the compound of general At this point in the synthesis, the protecting group on the pyrrolidine ring nitrogen atom is removed. Again, the deprotection is accomplished using iodine in a solution of tetrahydrofuran and water as described by Fraser-Reid et al. and the compound of general formula 22 ($R^8$=H) is produced. If it is desired that the $R^8$ substituent in the title compounds of general formula Ib be a group other than a hydrogen atom, then the $R^8$ substituent is then introduced.

Reaction Scheme 7 illustrates the two step process wherein the pentenoylamide protecting group of the compounds of general formula 21 is first removed and the resulting secondary amino group is reacted with a generalized alkylating, acylating, or sulfonylating reagent of general formula 15. In this example, the group X in compounds of general formula 15 indicates a leaving group such as a halide, mesylate, triflate or the like. However it is also within the scope of this invention that the $R^8$ substituent be incorporated into compounds of general formula 22 by other methods know in organic synthesis, for instance using reductive amination reactions with suitable carbonyl compounds, or using the palladium-catalyzed cross coupling reactions of amines described by Buchwald and others (Kienle, M.; Dubbaka, S. R.; Brade, K.; Knochel, P. *Eur. J. Org. Chem.* 2007, 25, 4166-76).

The final step in the synthesis of the novel compounds of general formula Ib is the conversion of the glycine ester of the intermediate of general formula 22 to the corresponding carboxylic acid. One useful method comprises selecting a glycine derivative of general formula 13 wherein the R group is a tert-butyl group. It is then possible to hydrolyze the glycinate of general formula 22 by treatment with an acid such as trifluoroacetic acid in a solvent like dichloromethane to afford a compound of general formula Ib. This reaction is typically conducted at room temperature or at slightly above room temperature and the reaction is conducted for periods of a few hours to overnight. If the substituent R present in the ester of general formula 22 is methyl, ethyl or the like, then a standard hydrolysis reaction under basic conditions converts the ester 22 to the glycineamide derivative of general formula Ib.

It should be also recognized that additional compounds of general formulae Ia and Ib that are within the scope of this invention may be synthesized using reactions known in the art of organic synthesis from one or more of the compounds presented in the preceding reaction schemes. For instance, reaction Scheme 8 illustrates a method wherein a cross-coupling reaction of an aryl or heteroaryl ring incorporated in one of the substituent groups $R^1$ through $R^8$ is used to incorporate an additional substituent. In this example, an aryl group present in the $R^1$ substituent of intermediates of general formulae 23a or 23b is reacted in a cross-coupling reaction with a suitable aryl or heteroaryl organometallic reagent of general formula 24. The preferred cross-coupling reactions include Suzuki, Stille, Negishi and similar cross-coupling reactions known in the art of organic synthesis. In these examples the group X designates a suitable leaving group such as a halide atom or a triflate, the group M in the coupling partner 24 designates a stannane, boronic acid, boronate ester or the like, and the products of these reactions are the derivatives of general formulae 25a and 25b incorporating a biaryl element within the $R^1$ substituent.

It is recognized that variants of the synthetic methods illustrated in reaction Scheme 8 are within the scope of this invention. For instance, one or both of the aryl groups in the newly formed biaryl element may be a heteroaryl ring as defined above. The compounds of general formula 25a or 25b are then converted into the title compounds of general formula Ia and Ib using the methods described previously.

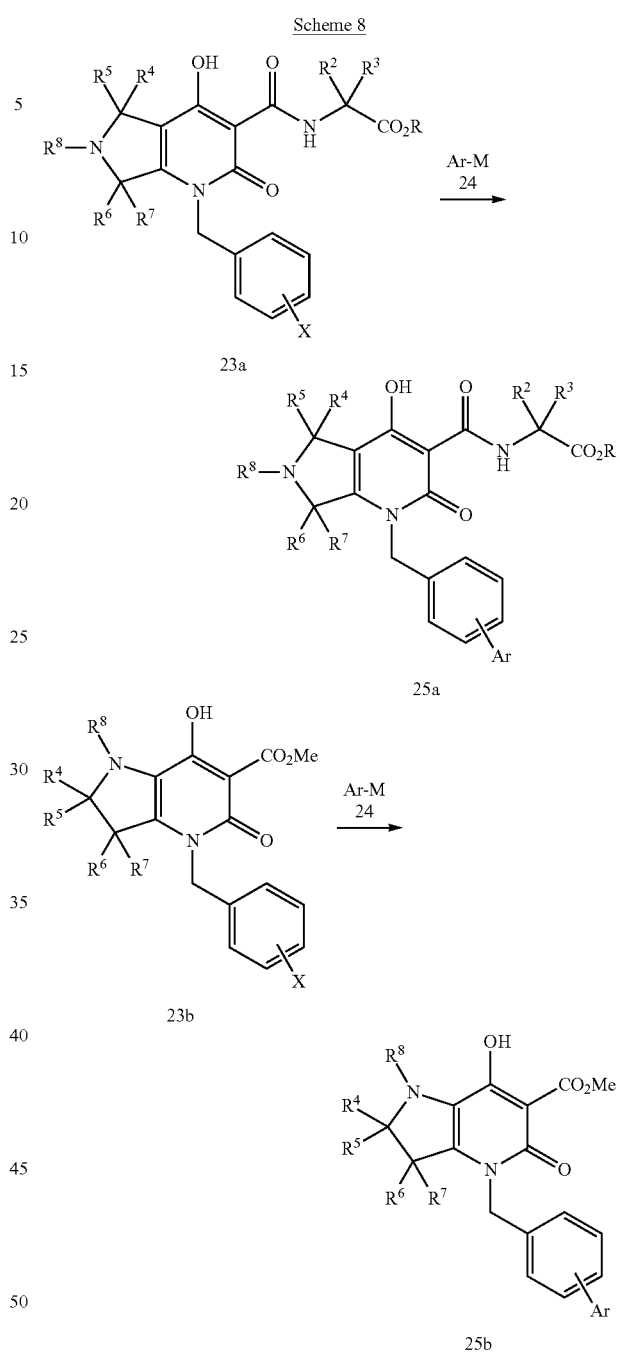

Scheme 8

General Experimental Comments

In the following examples, unless expressly stated otherwise, reactions sensitive to moisture or air were performed under nitrogen using anhydrous solvents and reagents as required. The progress of reactions was determined by either analytical thin layer chromatography (TLC) performed with E. MERCK precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm). Concentration of solutions was carried out on a rotary evaporator under reduced pressure.

Flash chromatography was performed using a Biotage Flash Chromatography apparatus (Dyax Corp.) on silica gel (32-63 mM, 60 Å pore size) in pre-packed cartridges. Abbreviations: acetic acid (AcOH), aqueous (aq), 1,1'-bis(diphenylphosphino)ferrocene (dppf), Et (ethyl), ethanol (EtOH), ethyl acetate (EtOAc), diethyl ether (ether or Et$_2$O), N,N-diisopropylethylamine (DIEA), N,N-dimethylformamide (DMF), 1,8-diazabicyclo[5.4.0]undec-7-ene (DBU), 4-N,N-dimethylaminopyridine (DMAP), NaOEt (sodium ethoxide), NaOMe (sodium methoxide), dimethyl sulfoxide (DMSO), gram(s) (g), hour(s) (h or hr), microliter(s) (μL), milligram(s) (mg), milliliter(s) (mL), millimole (mmol), mass spectrum (ms or MS), 2-propanol (IPA), retention time (R$_t$), room temperature (rt), saturated aq sodium chloride solution (brine), trifluoroacetic acid (TFA), tetrahydrofuran (THF), and minute(s) (min). Chiral analytical chromatography was performed on one of Chiralpak IA, Chiralpak AS, Chiralpak AD, Chiralcel OD, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak IA, Chiralpak AS, Chiralpak AD, Chiralcel OD, or Chiralcel OJ columns (20×250 mm) (Daicel Chemical Industries, Ltd.) with desired isocratic solvent systems identified on chiral analytical chromatography.

Intermediate 1

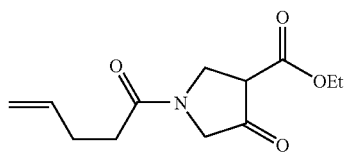

1-1

Ethyl 4-oxo-1-pent-4-enoylpyrrolidine-3-carboxylate. (1-1)

Step A: Ethyl N-(2-ethoxy-2-oxoethyl)-β-alaninate (1-a)

To ethyl glycinate hydrochloride (12.9 g, 92 mmol) in water (20 mL) at 0° C. was added cold aqueous NaOH (19.5 mL, 93 mmol, 4.75 M) followed by ethyl acrylate (9.18 g, 92 mmol). The reaction stirred about 18 hours and warmed to room temperature. The mixture was extracted with CH$_2$Cl$_2$ four times and the solution was dried (Na$_2$SO$_4$). The material was distilled at about 110° C. (1.8 torr) to afford the product, 1-a.

Step B: Ethyl N-(2-ethoxy-2-oxoethyl)-N-pent-4-enoyl-β-alaninate (1-b)

To the product of Step A, 1-a, (5.10 g, 25.1 mmol) in CH$_2$Cl$_2$ (50 mL) was added pent-4-enoyl chloride (2.83 mL, 25.1 mmol, 98% purity) and NEt$_3$ (4.20 mL, 30.1 mmol) at 5° C. The reaction stirred about 18 hours and was then diluted with CH$_2$Cl$_2$, washed with aq Na$_2$CO$_3$ (2 M) and brine, dried (Na$_2$SO$_4$), filtered and concentrated to afford the product, 1-b.

Step C: Ethyl 4-oxo-1-pent-4-enoylpyrrolidine-3-carboxylate 1-1

To the product of Step B, 1-b, (7.06 g, 24.7 mmol) in EtOH (40 mL) was added NaOEt (20.3 mL, 54.4 mmol, 21 wt in EtOH). The reaction was heated to reflux for 3 h and then cooled before the addition of aq HCl (28 mL, 2 M) followed by dilution with EtOAc and brine. The solution was extracted three times with EtOAc and dried (Na$_2$SO$_4$) to afford the title compound, 1-1, which was used without further purification to prepare Intermediate 4. HPLC/MS: 240.1 (M+1); R$_t$=2.22 min.

Intermediate 2

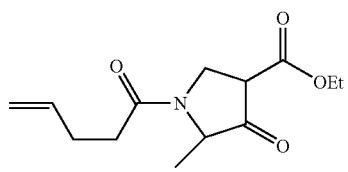

2-1

Ethyl 5-methyl-4-oxo-1-pent-4-enoylpyrrolidine-3-carboxylate 2-1

Using procedures similar to that of Intermediate 1, except using (±) ethyl alaninate hydrochloride instead of ethyl glycinate hydrochloride for Step A, the title compound was prepared. HPLC/MS: 254.1 (M+1); R$_t$=2.91 min.

Intermediate 3

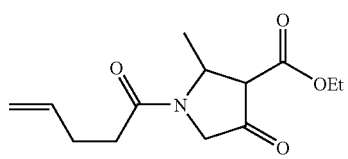

3-1

Ethyl 2-methyl-4-oxo-1-pent-4-enoylpyrrolidine-3-carboxylate 3-1

Using procedures similar to that of Intermediate 1, except using methyl crotonate instead of ethyl acrylate for Step A, the title compound was prepared. HPLC/MS: 254.0 (M+1); R$_t$=2.22 min.

Intermediate 4

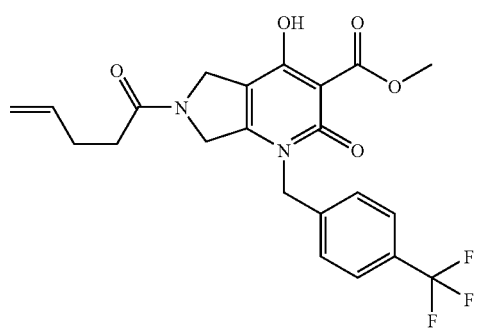

Methyl 4-hydroxy-2-oxo-6-pent-4-enoyl-1-[4-(trifluoromethyl)benzyl]-2,5,6,7-tetrahydro-1H-pyrrolo[3,4-b]pyridine-3-carboxylate 4-1

Step A: Ethyl 1-pent-4-enoyl-4-{[4-(trifluoromethyl)benzyl]amino}-2,5-dihydro-1H-pyrrole-3-carboxylate 4-a To the product of Intermediate 1 (5.79 g, 24.2 mmol) in EtOH (40 mL) was added 1-[4-(trifluoromethyl)phenyl]methanamine (3.58 mL, 24.2 mmol, 97% purity) and AcOH (0.277 mL, 4.84 mmol). The reaction was heated to reflux for about 100 min and was concentrated. The residue was diluted with EtOAc and washed with aq $Na_2CO_3$ (2 M) and brine. The concentrated residue was purified by flash chromatography on silica gel gradient eluted with 0-90% EtOAc/hexane to afford the product, 4-a.

Step B: Ethyl 4-{(3-methoxy-3-oxopropanoyl)[4-(trifluoromethyl)benzyl]amino}-1-pent-4-enoyl-2,5-dihydro-1H-pyrrole-3-carboxylate (4-b)

To the product of Step A, 4-a, (7.63 g, 19.3 mmol) in MeCN (35 mL) was added methyl 3-chloro-3-oxopropanoate (9.29 mL, 87.0 mmol) under a well purged $N_2$ atmosphere. The reaction stirred at 50° C. for 2 h 30 min and was then cooled. The reaction was diluted with EtOAc and washed with aq $Na_2CO_3$ (2 M) and brine. The concentrated residue was purified by flash chromatography on silica gel gradient eluted with 0-90% EtOAc/hexane to afford the product.

Step C: Methyl 4-hydroxy-2-oxo-6-pent-4-enoyl-1-[4-(trifluoromethyl)benzyl]-2,5,6,7-tetrahydro-1H-pyrrolo[3,4-b]pyridine-3-carboxylate (4-1)

To the product of Step B, 4-b, (6.30 g, 12.7 mmol) in MeOH (50 mL) was added NaOMe (4.35 mL, 19.0 mmol, 25 wt % in MeOH) at rt. After about 15 min the reaction was concentrated and the residue was diluted with EtOAc and washed with aq HCl (2 M) and brine. The material was crystallized from EtOAc and hexane to afford the title compound, 4-1. HPLC/MS: 451.0 (M+1); $R_t$=3.33 min.

Intermediate 5

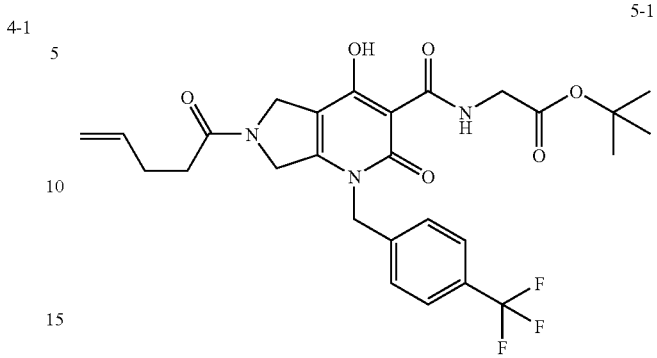

tert-Butyl N-({4-hydroxy-2-oxo-6-pent-4-enoyl-1-[4-(trifluoromethyl)benzyl]-2,5,6,7-tetrahydro-1H-pyrrolo[3,4-b]pyridin-3-yl}carbonyl)glycinate 5-1

To the product of Intermediate 4 (2.61 g, 5.79 mmol) in 1-propanol (36 mL) was added tert-butyl glycinate (1.58 mL, 11.6 mmol). The reaction refluxed 1 h and was then cooled and concentrated. The residue was purified by flash chromatography on silica gel gradient eluted with 0-85% EtOAc/hexane to afford the title compound, 5-1 HPLC/MS: 550.1 (M+1); $R_t$=3.85 min.

Intermediate 6

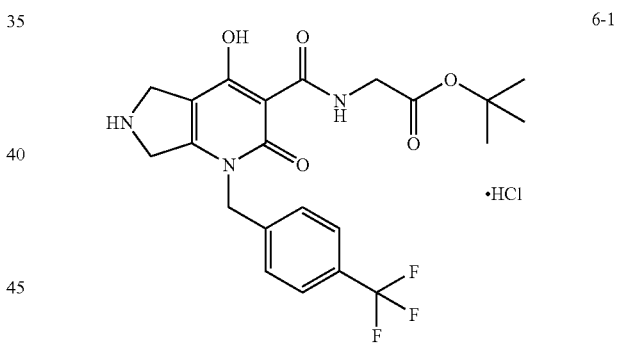

tert-Butyl N-({4-hydroxy-2-oxo-1-[4-(trifluoromethyl)benzyl]-2,5,6,7-tetrahydro-1H-pyrrolo[3,4-b]pyridin-3-yl}carbonyl)glycinate hydrochloride 6-1

To the product of Intermediate 5 (1.53 g, 2.78 mmol) in THF (30 mL) and water (15.5 mL) was added iodine (2.12 g, 8.35 mmol) at room temperature. The reaction stirred 30 min and was then quenched with $Na_2S_2O_3$ (color change). The solution was diluted with sat. aq $NaHCO_3$ to maintain near neutral pH. The solution was extracted with EtOAc, dried ($Na_2SO_4$), and concentrated. The residue was purified by flash chromatography on silica gel gradient eluted with 0-100% EtOAc/hexane followed by 0-15% MeOH/EtOAc to afford the product. The concentrated product was diluted with EtOAc and treated with 1 equivalent of HCl in dioxane. The mixture was concentrated to afford the title compound, 6-1. HPLC/MS: 468.0 (M+1); $R_t$=2.99 min.

Example 1

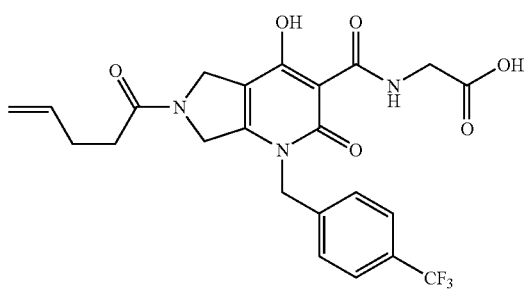

N-({4-hydroxy-2-oxo-6-pent-4-enoyl-1-[4-(trifluoromethyl)benzyl]-2,5,6,7-tetrahydro-1H-pyrrolo[3,4-b]pyridin-3-yl}carbonyl)glycine (E1-1)

To the product of Intermediate 5 (112 mg, 0.204 mmol) in $CH_2Cl_2$ (0.7 mL) was added TFA (1.5 mL) at rt. The reaction stirred 25 min and was concentrated. The product was solidified with $Et_2O$ and hexane. The solution was decanted away and the solid was washed with hexane to afford the title compound, E1-1. HPLC/MS: 494.0 (M+1); $R_t$=3.29 min.

Using synthesis strategies analogous to those of Intermediate 1 through Intermediate 5 and Example 1 along with the appropriate amine in Step A of Intermediate 4's procedure Examples 2 through 4 were prepared as shown in Table 1.

TABLE 1

| Example | Name | HPLC/MS m/z (M + 1) $R_t$ (min) | Structure |
|---|---|---|---|
| Example 2 | N-{[1-(biphenyl-4-ylmethyl)-4-hydroxy-2-oxo-6-pent-4-enoyl-2,5,6,7-tetrahydro-1H-pyrrolo[3,4-b]pyridin-3-yl]carbonyl}glycine | 502.1<br>3.42 | 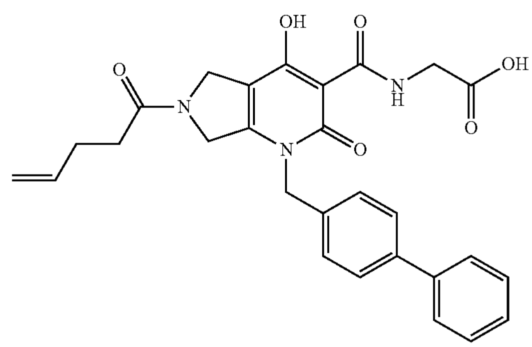 [SMILES: C=CCCC(=O)N1Cc2c(O)c(C(=O)NCC(=O)O)c(=O)n(Cc3ccc(-c4ccccc4)cc3)c2C1] |
| Example 3 | N-{[1-(1,3-benzothiazol-2-ylmethyl)-4-hydroxy-2-oxo-6-pent-4-enoyl-2,5,6,7-tetrahydro-1H-pyrrolo[3,4-b]pyridin-3-yl]carbonyl}glycine | 483.1<br>3.13 | 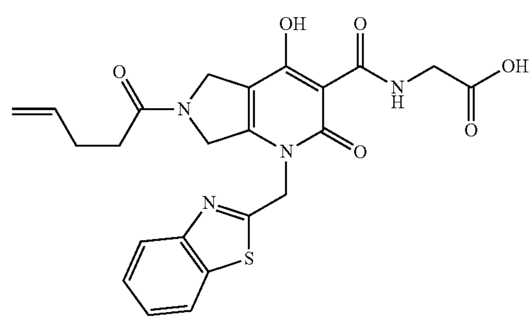 [SMILES: C=CCCC(=O)N1Cc2c(O)c(C(=O)NCC(=O)O)c(=O)n(Cc3nc4ccccc4s3)c2C1] |
| Example 4 | N-{[1-(3-bromobenzyl)-4-hydroxy-2-oxo-6-pent-4-enoyl-2,5,6,7-tetrahydro-1H-pyrrolo[3,4-b]pyridin-3-yl]carbonyl}glycine | 505.8<br>3.01 | 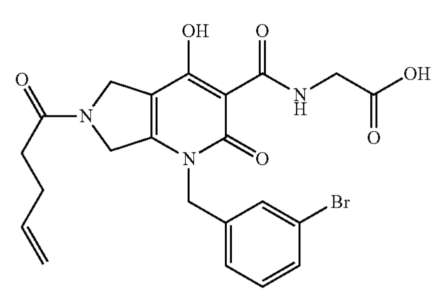 [SMILES: C=CCCC(=O)N1Cc2c(O)c(C(=O)NCC(=O)O)c(=O)n(Cc3cccc(Br)c3)c2C1] |

Example 5

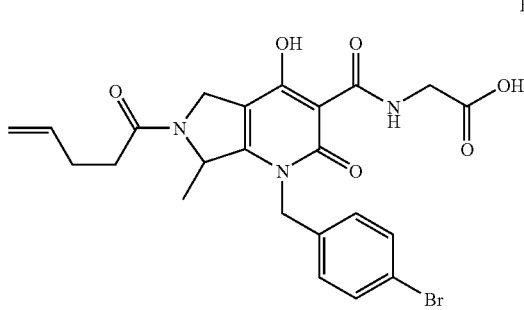

N-{[1-(4-bromobenzyl)-4-hydroxy-7-methyl-2-oxo-6-pent-4-enoyl-2,5,6,7-tetrahydro-1H-pyrrolo[3,4-b]pyridin-3-yl]carbonyl}glycine (E5-1)

The title compound was prepared using procedures similar to that of Example 1, starting with Intermediate 2 and utilizing 4-bromobenzylamine hydrochloride in step A of Intermediate 4 instead of 1-[4-(trifluoromethyl)pheny]methanamine. HPLC/MS: 519.8 (M+1); $R_t$=3.11 min.

Example 6

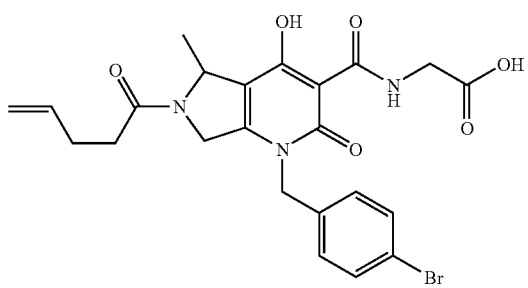

N-{[1-(4-bromobenzyl)-4-hydroxy-5-methyl-2-oxo-6-pent-4-enoyl-2,5,6,7-tetrahydro-1H-pyrrolo[3,4-b]pyridin-3-yl]carbonyl}glycine (E6-1)

The title compound, E6-1, was prepared using procedures similar to that of Example 1, starting with Intermediate 3 and utilizing 4-bromobenzylamine hydrochloride in step A of Intermediate 4 instead of 1-[4-(trifluoromethyl)pheny]methanamine. HPLC/MS: 520.0 (M+1); $R_t$=3.13 min.

Example 7

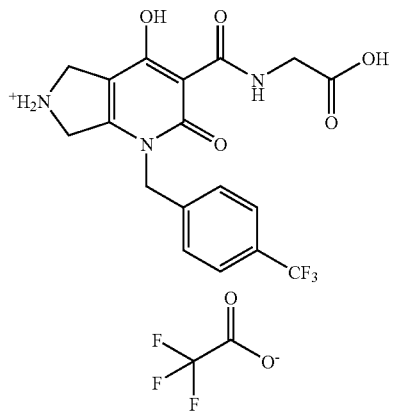

N-({4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate (E7-1)

To the product of Intermediate 6 (used as the free base) (25.5 mg, 0.55 mmol) in $CH_2Cl_2$ (0.2 mL) was added TFA (0.6 mL). The reaction was stirred at 30° C. for 50 min and was then concentrated. The material is crystallized with $Et_2O$ to afford the product, E7-1. HPLC/MS: 412.0 (M+1); $R_t$=2.32 min.

Example 8

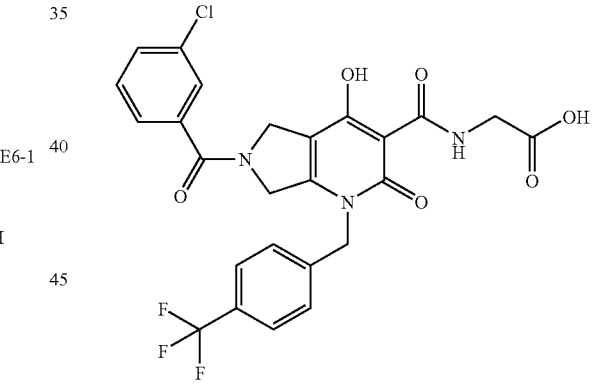

N-({6-(3-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine (E8-1)

Intermediate 6 (30 mg, 0.06 mmol) was dissolved in DCM (1 mL) and 3-chlorobenzoyl chloride (10.5 mg, 8 mL, 0.06 mmol) and DIEA (21 uL, 0.12 mmol) were added. The reaction was stirred at ambient temperature for 15 min. TFA (0.5 mL, 6.5 mmol) was added and the solution was stirred an additional 15 min. The reaction was concentrated and the residue was diluted in ether. The resulting precipitate was isolated affording the title compound, E8-1. 550.0 (M+1); $R_t$=3.45 min.

Using the procedure similar to that described in Example 8 and the appropriate acid chloride, sulfonoyl chloride, carbamoyl chloride, chloroformate or sulfamoyl chloride, the following compounds, Examples 9-21 were prepared as tabulated in Table 2.

TABLE 2

| Example | Name | HPLC/MS m/z (M + 1) R$_t$ (min) | Structure |
|---|---|---|---|
| Example 9 | N-({6-acetyl-4-hydroxy-2-oxo-1-[4-(trifluoromethyl)benzyl]-2,5,6,7-tetrahydro-1H-pyrrolo[3,4-b]pyridin-3-yl}carbonyl)glycine | 454.0<br>2.93 | 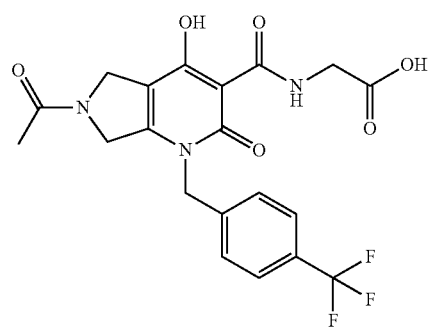 [SMILES: CC(=O)N1Cc2c(O)c(C(=O)NCC(=O)O)c(=O)n(Cc3ccc(C(F)(F)F)cc3)c2C1] |
| Example 10 | N-({4-hydroxy-6-(methylsulfonyl)-2-oxo-1-[4-(trifluoromethyl)benzyl]-2,5,6,7-tetrahydro-1H-pyrrolo[3,4-b]pyridin-3-yl}carbonyl)glycine | 489.9<br>3.09 | 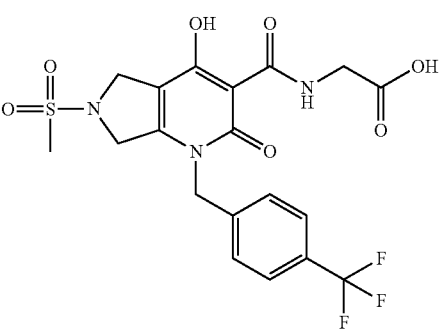 [SMILES: CS(=O)(=O)N1Cc2c(O)c(C(=O)NCC(=O)O)c(=O)n(Cc3ccc(C(F)(F)F)cc3)c2C1] |
| Example 11 | N-({4-hydroxy-6-(morpholin-4-ylcarbonyl)-2-oxo-1-[4-(trifluoromethyl)benzyl]-2,5,6,7-tetrahydro-1H-pyrrolo[3,4-b]pyridin-3-yl}carbonyl)glycine | 525.0<br>3.08 | 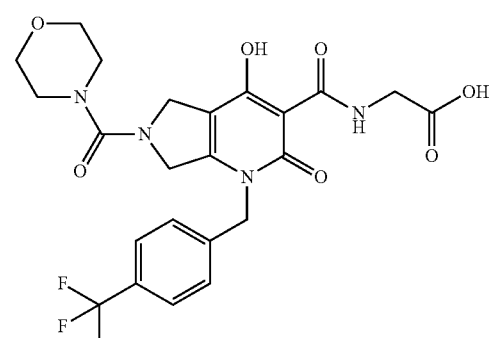 |
| Example 12 | N-({6-[(dimethylamino)sulfonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine | 518.9<br>3.25 | 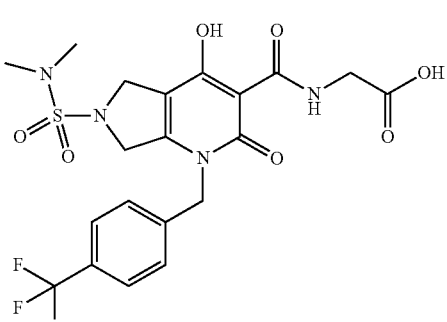 |

TABLE 2-continued

| Example | Name | HPLC/MS m/z (M + 1) R$_t$ (min) | Structure |
| --- | --- | --- | --- |
| Example 13 | N-({6-(cyclopropylcarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine | 480.0 3.17 | 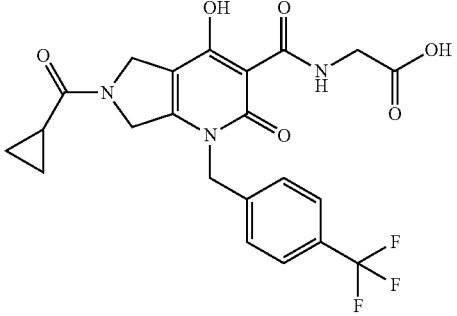 [SMILES: O=C(O)CNC(=O)c1c(O)c2c(n(Cc3ccc(C(F)(F)F)cc3)c1=O)CN(C(=O)C1CC1)C2] |
| Example 14 | N-({4-hydroxy-6-(methoxyacetyl)-2-oxo-1-[4-(trifluoromethyl)benzyl]-2,5,6,7-tetrahydro-1H-pyrrolo[3,4-b]pyridin-3-yl}carbonyl)glycine | 484.0 2.95 | 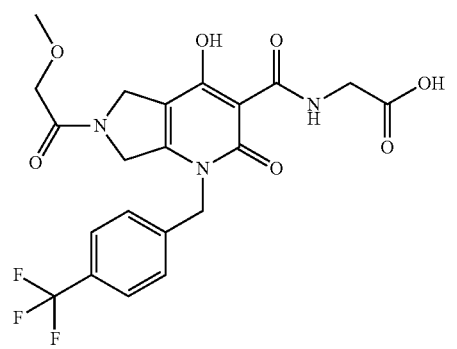 [SMILES: COCC(=O)N1Cc2c(O)c(C(=O)NCC(=O)O)c(=O)n(Cc3ccc(C(F)(F)F)cc3)c2C1] |
| Example 15 | N-({6-(2,2-dimethylpropanoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine | 496.3 3.20 | 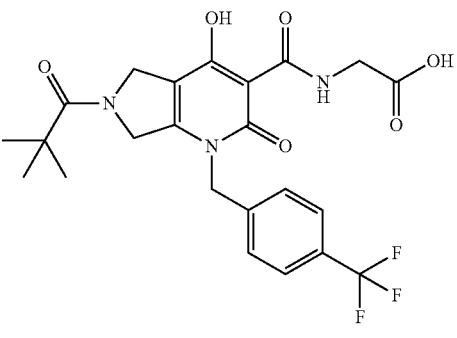 [SMILES: CC(C)(C)C(=O)N1Cc2c(O)c(C(=O)NCC(=O)O)c(=O)n(Cc3ccc(C(F)(F)F)cc3)c2C1] |
| Example 16 | N-({6-(ethoxycarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine | 483.9 3.32 | 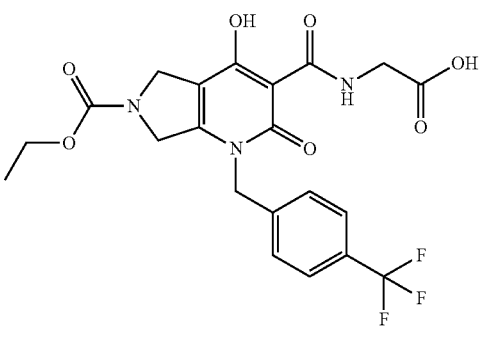 [SMILES: CCOC(=O)N1Cc2c(O)c(C(=O)NCC(=O)O)c(=O)n(Cc3ccc(C(F)(F)F)cc3)c2C1] |

TABLE 2-continued

| Example | Name | HPLC/MS m/z (M + 1) R$_t$ (min) | Structure |
|---|---|---|---|
| Example 17 | N-({4-hydroxy-2-oxo-6-(pyrrolidin-1-ylcarbonyl)-1-[4-(trifluoromethyl)benzyl]-2,5,6,7-tetrahydro-1H-pyrrolo[3,4-b]pyridin-3-yl}carbonyl)glycine | 509.0 3.25 | 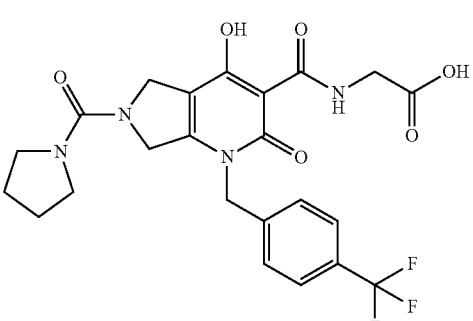 |
| Example 18 | N-({6-(2-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine | 550.0 3.37 | 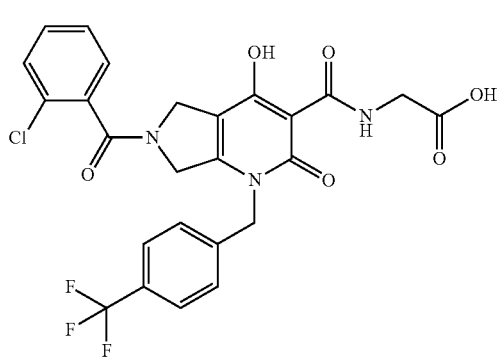 [SMILES: O=C(O)CNC(=O)c1c(O)c2c(n(Cc3ccc(C(F)(F)F)cc3)c1=O)CN(C(=O)c1ccccc1Cl)C2] |
| Example 19 | N-({4-hydroxy-2-oxo-6-(phenylsulfonyl)-1-[4-(trifluoromethyl)benzyl]-2,5,6,7-tetrahydro-1H-pyrrolo[3,4-b]pyridin-3-yl}carbonyl)glycine | 551.9 3.43 | 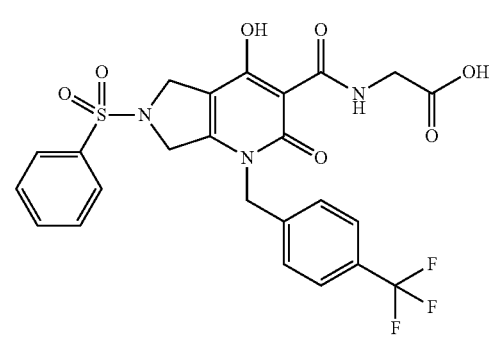 [SMILES: O=C(O)CNC(=O)c1c(O)c2c(n(Cc3ccc(C(F)(F)F)cc3)c1=O)CN(S(=O)(=O)c1ccccc1)C2] |
| Example 20 | N-({6-(cyclopentylcarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine | 508.0 3.40 | 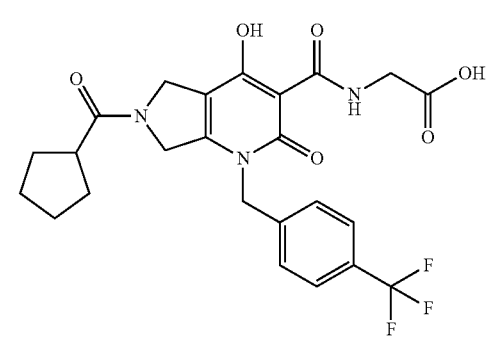 [SMILES: O=C(O)CNC(=O)c1c(O)c2c(n(Cc3ccc(C(F)(F)F)cc3)c1=O)CN(C(=O)C1CCCC1)C2] |

TABLE 2-continued

| Example | Name | HPLC/MS m/z (M + 1) R_t (min) | Structure |
|---|---|---|---|
| Example 21 | N-({6-(4-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine | 550.0<br>3.46 | 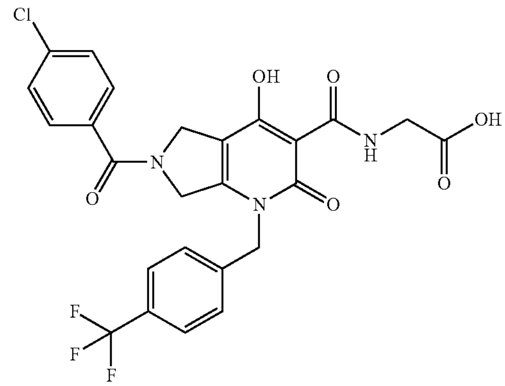 [SMILES: O=C(O)CNC(=O)c1c(O)c2c(n(Cc3ccc(C(F)(F)F)cc3)c1=O)CN(C(=O)c1ccc(Cl)cc1)C2] |

Using the product of Example 2, E2-1, and procedures described in Example 7 and Example 8 the following compounds were prepared:

TABLE 3

| Example 22 | N-{[1-(biphenyl-4-ylmethyl)-6-(ethoxycarbonyl)-4-hydroxy-2-oxo-2,5,6,7-tetrahydro-1H-pyrrolo[3,4-b]pyridin-3-yl]carbonyl}glycine | 492.1<br>3.50 | |

Example 23

N-({6-[(1,3-dimethyl-1H-pyrazol-5-yl)carbonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine, E23-1)

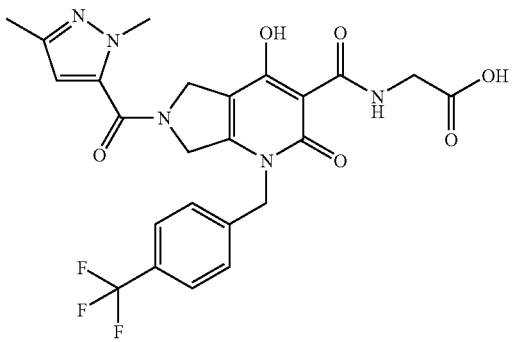

E23-1

Intermediate 6, 6-1, (30 mg, 0.06 mmol) was dissolved in DMA (1 mL) and 1,3-dimethyl-1H-pyrazole-5-carboxylic acid (13.5 mg, 0.096 mmol), PyBOP (40 mg, 0.077 mmol) and DIPEA (16.5 mg, 22 uL, 0.13 mmol) were added and the reaction was stirred for 15 min. The mixture was diluted in EtOAc and washed with brine and aq HCl (2M), dried (Na$_2$SO$_4$), filtered and concentrated. The resulting mixture was dissolved in DCM (1 mL) and TFA (0.5 mL, 6.5 mmol) was added. The reaction was stirred for 30 min and concentrated. The residue was diluted with ether and the resulting precipitate was isolated affording the title compound, E23-1. 534.0 (M+1); R$_t$=3.18 min.

Using the procedure analogous to that described in Example 23 and the appropriate carboxylic acid the following compounds, Examples 24 through 37 were prepared as found in Table 4.

TABLE 4

| Example | Name | HPLC/MS m/z (M + 1) R$_t$ (min) | Structure |
|---|---|---|---|
| Example 24 | N-({4-hydroxy-2-oxo-6-(pyrazolo[1,5-a]pyrimidin-2-ylcarbonyl)-1-[4-(trifluoromethyl)benzyl]-2,5,6,7-tetrahydro-1H-pyrrolo[3,4-b]pyridin-3-yl}carbonyl)glycine | 557.0<br>3.15 | 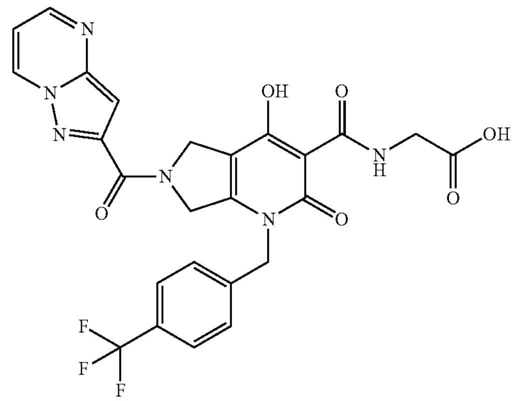 [SMILES: O=C(O)CNC(=O)c1c(O)c2c(n(Cc3ccc(C(F)(F)F)cc3)c1=O)CN(C(=O)c1cc3ncccn3n1)C2] |
| Example 25 | N-({4-hydroxy-2-oxo-6-(pyridin-3-ylcarbonyl)-1-[4-(trifluoromethyl)benzyl]-2,5,6,7-tetrahydro-1H-pyrrolo[3,4-b]pyridin-3-yl}carbonyl)glycine | 517.0<br>2.78 | 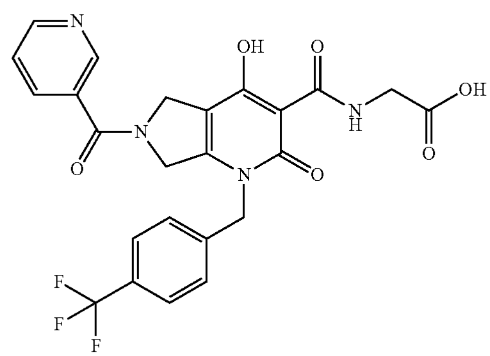 [SMILES: O=C(O)CNC(=O)c1c(O)c2c(n(Cc3ccc(C(F)(F)F)cc3)c1=O)CN(C(=O)c1cccnc1)C2] |
| Example 26 | N-({4-hydroxy-6-[(6-methylpyridin-3-yl)carbonyl]-2-oxo-1-[4-(trifluoromethyl)benzyl]-2,5,6,7-tetrahydro-1H-pyrrolo[3,4-b]pyridin-3-yl}carbonyl)glycine | 531.0<br>2.68 | 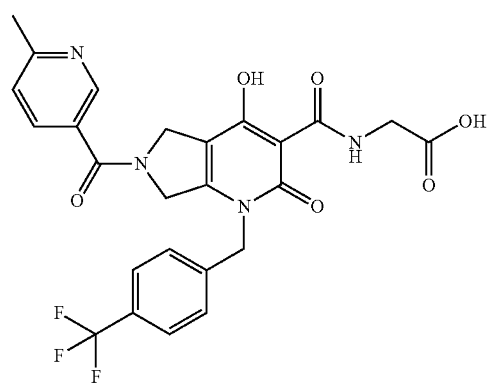 [SMILES: Cc1ccc(C(=O)N2Cc3c(O)c(C(=O)NCC(=O)O)c(=O)n(Cc4ccc(C(F)(F)F)cc4)c3C2)cn1] |
| Example 27 | N-({4-hydroxy-6-(1-methyl-L-prolyl)-2-oxo-1-[4-(trifluoromethyl)benzyl]-2,5,6,7-tetrahydro-1H-pyrrolo[3,4-b]pyridin-3-yl}carbonyl)glycine | 523.1<br>2.55 | 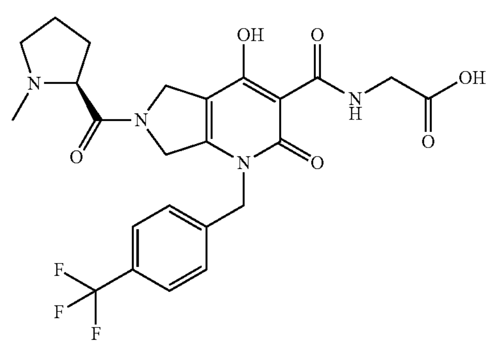 [SMILES: CN1CCC[C@H]1C(=O)N1Cc2c(O)c(C(=O)NCC(=O)O)c(=O)n(Cc3ccc(C(F)(F)F)cc3)c2C1] |

TABLE 4-continued

| Example | Name | HPLC/MS m/z (M + 1) R$_t$ (min) | Structure |
|---|---|---|---|
| Example 28 | N-({4-hydroxy-2-oxo-6-(5-oxo-L-prolyl)-1-[4-(trifluoromethyl)benzyl]-2,5,6,7-tetrahydro-1H-pyrrolo[3,4-b]pyridin-3-yl}carbonyl)glycine | 523.1 2.78 | 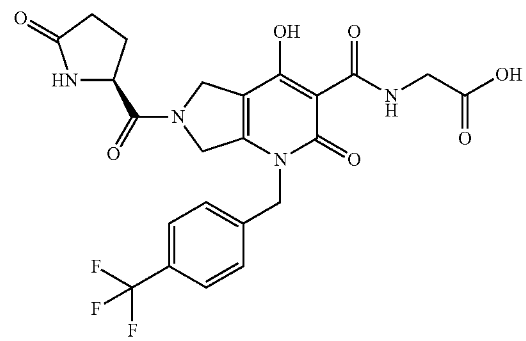 [SMILES: O=C(O)CNC(=O)c1c(O)c2c(n(Cc3ccc(C(F)(F)F)cc3)c1=O)CN(C(=O)[C@@H]1CCC(=O)N1)C2] |
| Example 29 | N-({4-hydroxy-2-oxo-6-(1,3-thiazol-4-ylcarbonyl)-1-[4-(trifluoromethyl)benzyl]-2,5,6,7-tetrahydro-1H-pyrrolo[3,4-b]pyridin-3-yl}carbonyl)glycine | 523.0 3.19 | 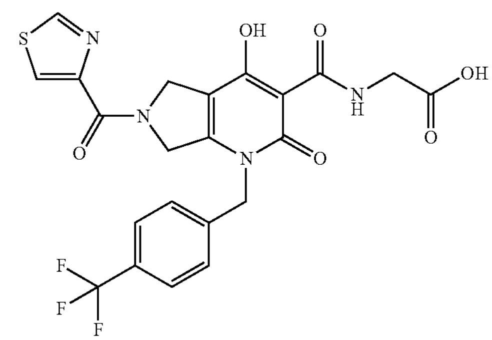 [SMILES: O=C(O)CNC(=O)c1c(O)c2c(n(Cc3ccc(C(F)(F)F)cc3)c1=O)CN(C(=O)c1cscn1)C2] |
| Example 30 | N-({4-hydroxy-2-oxo-6-(1,3-thiazol-5-ylcarbonyl)-1-[4-(trifluoromethyl)benzyl]-2,5,6,7-tetrahydro-1H-pyrrolo[3,4-b]pyridin-3-yl}carbonyl)glycine | 523.0 3.07 | 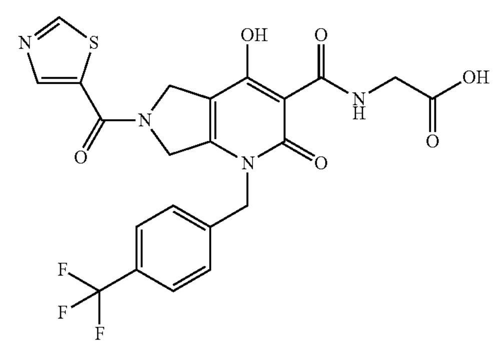 [SMILES: O=C(O)CNC(=O)c1c(O)c2c(n(Cc3ccc(C(F)(F)F)cc3)c1=O)CN(C(=O)c1cncs1)C2] |
| Example 31 | N-({6-[(1,5-dimethyl-1H-pyrazol-2-ium-3-yl)carbonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine chloride | 534.1 3.25 | 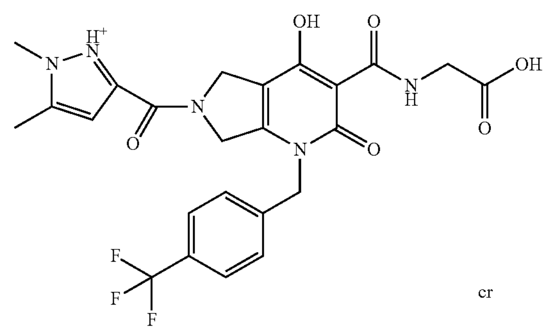 |

TABLE 4-continued

| Example | Name | HPLC/MS m/z (M + 1) R$_t$ (min) | Structure |
|---|---|---|---|
| Example 32 | N-({4-hydroxy-6-{[(2S)-1-methylpyrrolidinium-2-yl]carbonyl}-2-oxo-1-[4-(trifluoromethyl)benzyl]-2,5,6,7-tetrahydro-1H-pyrrolo[3,4-b]pyridin-3-yl}carbonyl)glycine trifluoroacetate | 523.1 2.55 | 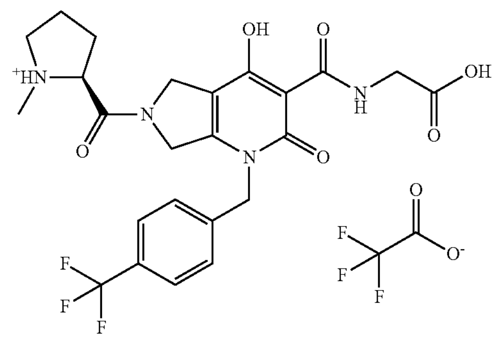 [SMILES: C[NH+]1CCC[C@H]1C(=O)N1Cc2c(O)c(C(=O)NCC(=O)O)c(=O)n(Cc3ccc(C(F)(F)F)cc3)c2C1 ; O=C([O-])C(F)(F)F] |
| Example 33 | N-({4-hydroxy-6-(isoxazol-5-ylcarbonyl)-2-oxo-1-[4-(trifluoromethyl)benzyl]-2,5,6,7-tetrahydro-1H-pyrrolo[3,4-b]pyridin-3-yl}carbonyl)glycine | 507.0 3.04 | 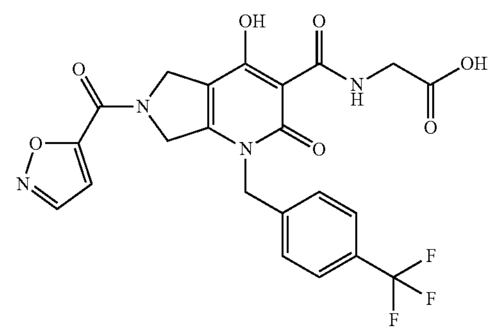 [SMILES: O=C(O)CNC(=O)c1c(O)c2c(n(Cc3ccc(C(F)(F)F)cc3)c1=O)CN(C(=O)c1ccno1)C2] |
| Example 34 | N-({4-hydroxy-2-oxo-6-(1,3-thiazol-2-ylcarbonyl)-1-[4-(trifluoromethyl)benzyl]-2,5,6,7-tetrahydro-1H-pyrrolo[3,4-b]pyridin-3-yl}carbonyl)glycine | 523.0 3.32 | 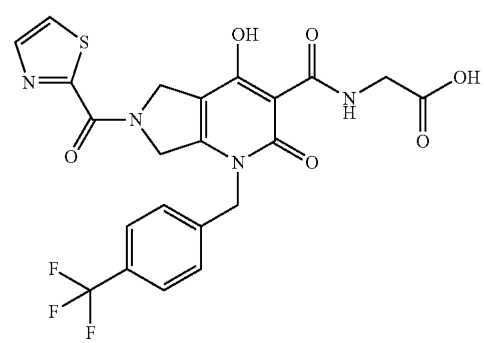 [SMILES: O=C(O)CNC(=O)c1c(O)c2c(n(Cc3ccc(C(F)(F)F)cc3)c1=O)CN(C(=O)c1nccs1)C2] |
| Example 35 | N-({4-hydroxy-2-oxo-6-(1,2,3-thiadiazol-4-ylcarbonyl)-1-[4-(trifluoromethyl)benzyl]-2,5,6,7-tetrahydro-1H-pyrrolo[3,4-b]pyridin-3-yl}carbonyl)glycine | 524.1 3.18 | 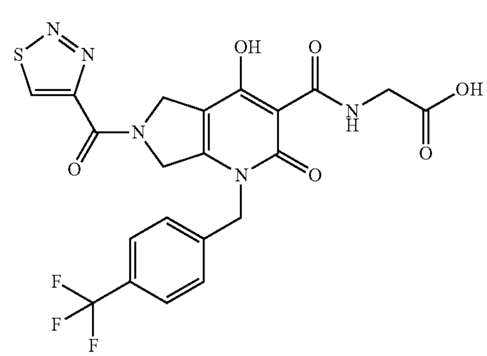 [SMILES: O=C(O)CNC(=O)c1c(O)c2c(n(Cc3ccc(C(F)(F)F)cc3)c1=O)CN(C(=O)c1csnn1)C2] |

TABLE 4-continued

| Example | Name | HPLC/MS m/z (M + 1) R$_t$(min) | Structure |
|---|---|---|---|
| Example 36 | N-({4-hydroxy-6-[(6-methylpyridinium-3-yl)carbonyl]-2-oxo-1-[4-(trifluoromethyl)benzyl]-2,5,6,7-tetrahydro-1H-pyrrolo[3,4-b]pyridin-3-yl}carbonyl)glycine trifluoroacetate | 530.9 2.45 | 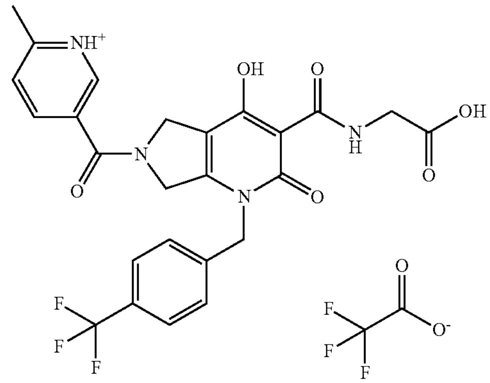 [SMILES: Cc1ccc(C(=O)N2Cc3c(O)c(C(=O)NCC(=O)O)c(=O)n(Cc4ccc(C(F)(F)F)cc4)c3C2)c[nH+]1 ; O=C([O-])C(F)(F)F] |
| Example 37 | N-({4-hydroxy-6-(1,3-oxazol-4-ylcarbonyl)-2-oxo-1-[4-(trifluoromethyl)benzyl]-2,5,6,7-tetrahydro-1H-pyrrolo[3,4-b]pyridin-3-yl}carbonyl)glycine | 506.8 2.85 | 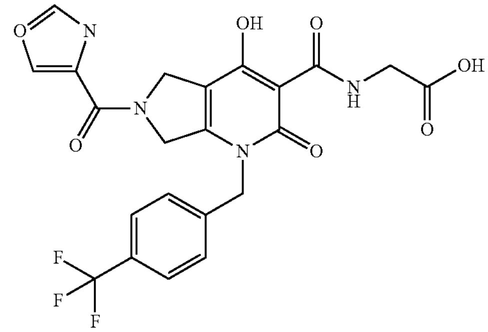 |

Using tert-butyl N-{[1-(biphenyl-4-ylmethyl)-4-hydroxy-2-oxo-2,5,6,7-tetrahydro-1H-pyrrolo[3,4-b]pyridin-3-yl]carbonyl}glycinate hydrochloride (prepared in similar fashion to Intermediate 6, 6-1) and a procedure analogous to that described for the preparation of Example 23 the following compound, Example 38 was prepared as shown in Table 5.

TABLE 5

| | | | |
|---|---|---|---|
| Example 38 | N-{[1-(biphenyl-4-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine | 530.8 3.15 | |

Example 39

E39-1

N-({6-(4-chlorobenzyl)-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate (E39-1)

Intermediate 6, compound 6-1, (50 mg, 0.11 mmol) was dissolved in DCM (1 mL) and 4-chlorobenzylbromide (22 mg, 0.11 mmol) and TEA (0.045 mL, 0.32 mmol) were added and the mixture was refluxed for 24 h. The reaction was cooled to rt and TFA (0.5 mL, 6 mmol) was added and the solution was stirred an additional 30 min. The reaction was concentrated and the residue was purified on a C-18 reverse phase chromatography column eluted with 0-90% MeCN in water. The desired fractions were lyophilized overnight affording the title compound, E39-1. 535.8 (M+1); $R_t$=2.80 min.

Using synthesis techniques analogous to that of Example 39 and the appropriate starting materials the following compounds, Examples 40 through 41 were obtained as shown in Table 6.

Example 42

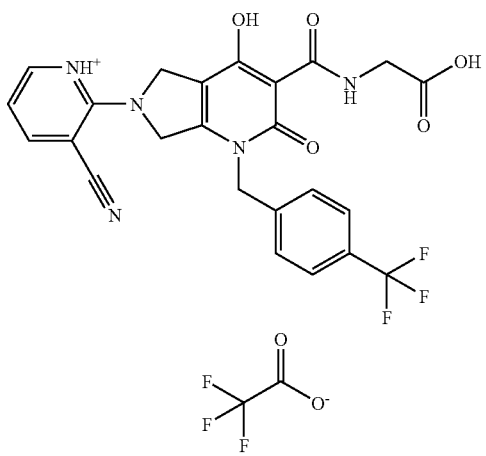

E42-1

TABLE 6

| Example | Name | HPLC/MS m/z (M + 1) $R_t$ (min) | Structure |
| --- | --- | --- | --- |
| Example 40 | N-({6-(3-chlorobenzyl)-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine chloride | 536.0<br>3.02 | 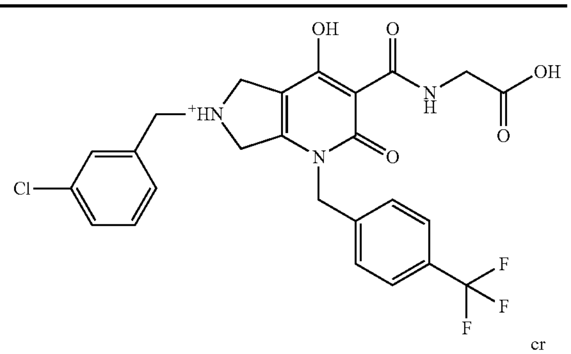 |
| Example 41 | N-({6-ethyl-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate | 440.0<br>2.44 | 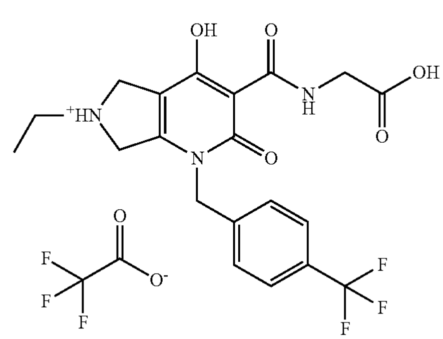 [SMILES: CC[NH+]1Cc2c(O)c(C(=O)NCC(=O)O)c(=O)n(Cc3ccc(C(F)(F)F)cc3)c2C1 ; O=C([O-])C(F)(F)F] |

N-({6-(3-cyanopyridinium-2-yl)-4-hydroxy-2-oxo-1-[4-(trifluoromethyl)benzyl]-2,5,6,7-tetrahydro-1H-pyrrolo[3,4-b]pyridin-3-yl}carbonyl)glycine trifluoroacetate (E42-1)

Step A: tert-butyl N-({6-(3-cyanopyridin-2-yl)-4-hydroxy-2-oxo-1-[4-trifluoromethyl)benzyl]-2,5,6,7-tetrahydro-1H-pyrrolo[3,4-b]pyridin-3-yl}carbonyl)glycinate (E42-a)

To the product of Intermediate 6, compound 6-1, (free base form) (32.0 mg, 0.068 mmol) was added DMA (0.75 mL), DIEA (0.36 mL, 0.205 mL), and 2-chloronicotinonitrile (9.5 mg, 0.068 mmol) in a CEM corporation microwave tube. The tube was then placed into a CEM Discover microwave reactor and heated to 120° C. for 12 min. The reaction was diluted with EtOAc and washed with brine. The concentrated residue was purified by semi-preparative reverse phase HPLC on a C18 column eluting with 15-100% MeCN/water (each with 0.05% TFA) to afford the product, E42-a.

Step B: N-({6-(3-cyanopyridinium-2-yl)-4-hydroxy-2-oxo-1-[4-(trifluoromethyl)benzyl]-2,5,6,7-tetrahydro-1H-pyrrolo[3,4-b]pyridin-3-yl}carbonyl)glycine trifluoroacetate (E42-b)

To all of the products of Step A in CH$_2$Cl$_2$ (1 mL) was added TFA (0.6 mL). The reaction was heated to 33° C. for 70 min and was then concentrated. The material was crystallized with Et$_2$O and washed with hexane to afford the title compound, E42-1. HPLC/MS: 514.0 (M+1); R$_t$=3.49 min.

Example 43

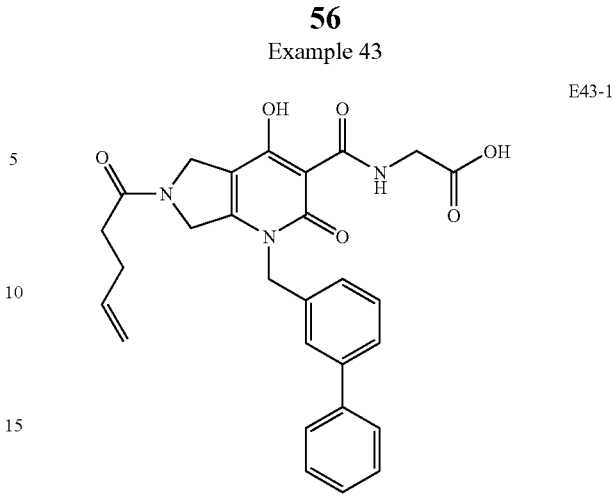

N-{[1-(biphenyl-3-ylmethyl)-4-hydroxy-2-oxo-6-pent-4-enoyl-2,5,6,7-tetrahydro-1H-pyrrolo[3,4-b]pyridin-3-yl]carbonyl}glycine (E43-1)

tert-Butyl N-{[1-(3-bromobenzyl)-4-hydroxy-2-oxo-6-pent-4-enoyl-2,5,6,7-tetrahydro-1H-pyrrolo[3,4-b]pyridin-3-yl]carbonyl}glycinate (50 mg, 0.09 mmol, prepared in similar fashion to Intermediate 5 (compound 5-1) was dissolved in DMA (2 mL) in a 10 mL reaction tube of a CEM Corporation Discover 300 Watt microwave reactor. Aqueaous Na$_2$CO$_3$ (2 M, 0.8 mL, 1.6 mmol), phenylboronic acid (20 mg, 0.16 mmol) and bis(triphenylphosphine)palladium(II) chloride (7 mg, 0.009 mmol) were added and the tube was purged with nitrogen, capped and inserted into the microwave reactor and heated at 115° C., for 15 min. The reaction was diluted with EtOAc, washed with 2 M HCl, dried (Na$_2$SO$_4$), filtered and concentrated. The residue was purified on a C-18 reverse phase chromatography column eluted with 0-100% MeCN in water. The desired fractions were concentrated, diluted with EtOAc and washed with 2 M HCl. The organic portion was isolated, dried (Na$_2$SO$_4$), filtered and concentrated affording the title compound, E43-1. HPLC/MS: 501.9 (M+1); R$_t$=3.22 min.

Using the appropriate starting material and a procedure analogous to that of Example 43 the compounds, Example 44 through 48 were prepared as found in Table 7.

TABLE 7

| Example | Name | HPLC/MS m/z (M + 1) R$_t$ (min) | Structure |
|---|---|---|---|
| Example 44 | N-{[1-(biphenyl-3-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine | 530.9 3.14 | 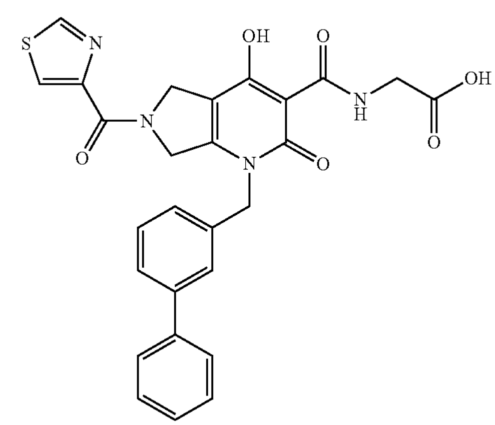 [SMILES: O=C(O)CNC(=O)c1c(O)c2c(n(Cc3cccc(-c4ccccc4)c3)c1=O)CN(C(=O)c1cscn1)C2] |

TABLE 7-continued

| Example | Name | HPLC/MS m/z (M + 1) R$_t$ (min) | Structure |
| --- | --- | --- | --- |
| Example 45 | N-{[1-[(4'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine | 564.8 3.31 | 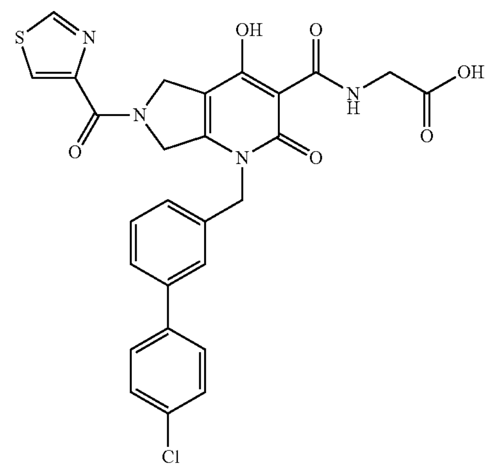 [SMILES: O=C(O)CNC(=O)c1c(O)c2c(n(Cc3cccc(-c4ccc(Cl)cc4)c3)c1=O)CN(C(=O)c1cscn1)C2] |
| Example 46 | N-{[4-hydroxy-2-oxo-1-(3-pyrimidin-5-ylbenzyl)-6-(1,3-thiazol-4-ylcarbonyl)-2,5,6,7-tetrahydro-1H-pyrrolo[3,4-b]pyridin-3-yl]carbonyl}glycine | 532.8 2.55 | 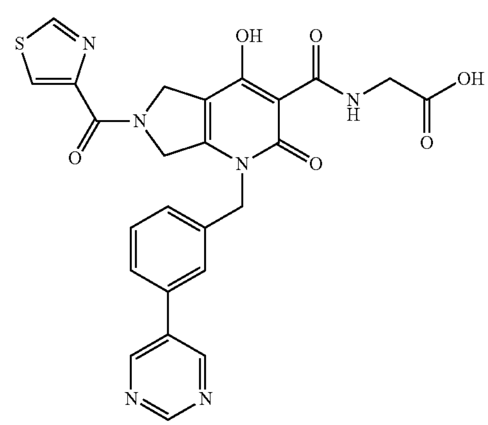 |

TABLE 7-continued

| Example | Name | HPLC/MS m/z (M + 1) R$_t$ (min) | Structure |
|---|---|---|---|
| Example 47 | N-{[1-[(2'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine | 564.8 3.19 | 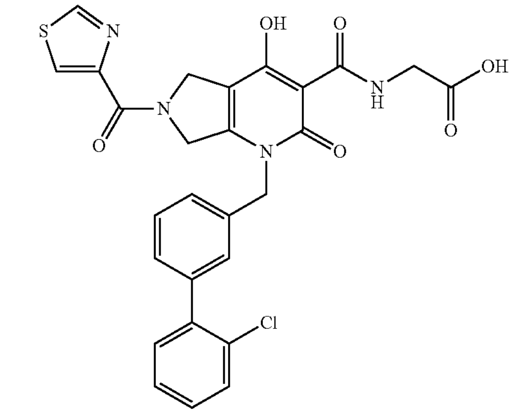 [SMILES: O=C(O)CNC(=O)c1c(O)c2c(n(Cc3cccc(-c4ccccc4Cl)c3)c1=O)CN(C(=O)c1cscn1)C2] |
| Example 48 | N-{[1-(biphenyl-4-ylmethyl)-4-hydroxy-7-methyl-2-oxo-6-pent-4-enoyl-2,5,6,7-tetrahydro-1H-pyrrolo[3,4-b]pyridin-3-yl]carbonyl}glycine | 515.0 3.30 | 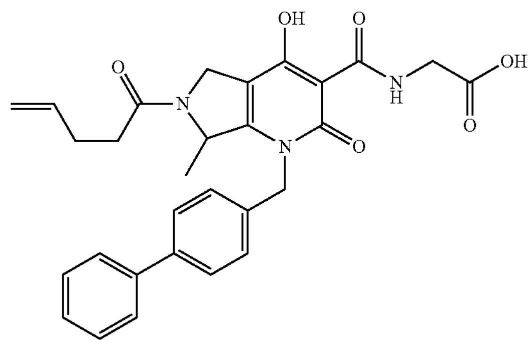 [SMILES: C=CCCC(=O)N1Cc2c(O)c(C(=O)NCC(=O)O)c(=O)n(Cc3ccc(-c4ccccc4)cc3)c2C1C] |

Example 49

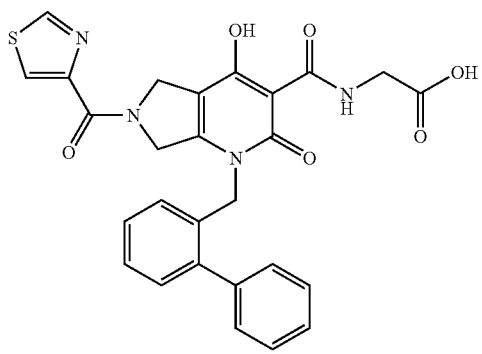

N-{[1-(biphenyl-2-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine (E49-1)

Step A

E49-a tert-Butyl N-{[1-(2-bromobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycinate (70 mg, 0.12 mmol, prepared in similar fashion to Intermediate 5, compound 5-1) was dissolved in DMA (1 mL) in a 10 mL reaction tube of a CEM Corporation Discover 300 Watt microwave reactor. Aq Na$_2$CO$_3$ (2 M, 0.12 mL, 0.24 mmol), phenylboronic acid (15 mg, 0.12 mmol) and bis(triphenylphosphine) palladium(II) chloride (8 mg, 0.012 mmol) were added and the tube was purged with nitrogen, capped and inserted into the microwave reactor and heated at 115° C., 20 watts maximum power, for 15 min. The reaction was diluted with EtOAc, washed with 2 M HCl, dried (Na$_2$SO$_4$), filtered and concentrated. The residue was purified on a silica flash chromatography column eluted with 0-40% EtOAc in hexanes. The desired fractions were concentrated affording the compound, E49-a.

Step B N-{[1-(biphenyl-2-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine (E49-b)

The product of Step A, compound E49-a, (30 mg, 0.05 mmol) was dissolved in DCM (1 mL) and TFA (1 mL, 13 mmol) was added. The reaction was stirred at ambient temperature for 2 h. The reaction was concentrated and the residue was purified on a C-18 reverse phase chromatography column eluted with 0-100% MeCN in water. The desired fractions were concentrated, diluted with EtOAc and washed with 2 M HCl. The organic portion was isolated, dried (Na$_2$SO$_4$), filtered and concentrated affording the title compound, E49-1. HPLC/MS: 531.1 (M+1); R$_t$=3.06 min.

Using the appropriate starting material and procedures analogous to those described in Example 49 the following compounds, Examples 50 through 53 were prepared as shown in Table 8.

TABLE 8

| Example | Name | HPLC/MS m/z (M + 1) R_t (min) | Structure |
|---------|------|-------------------------------|-----------|
| Example 50 | N-{[1-[(3'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine | 564.8 3.29 | 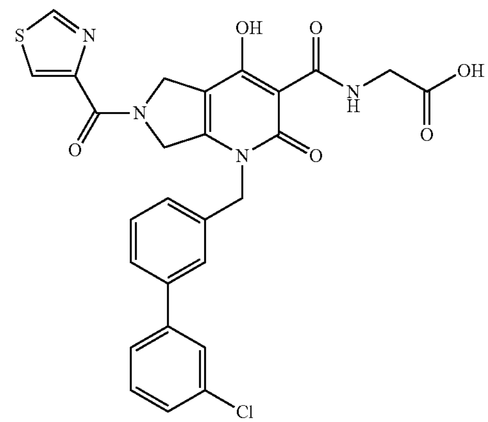 [SMILES: O=C(O)CNC(=O)c1c(O)c2c(n(Cc3cccc(-c4cccc(Cl)c4)c3)c1=O)CN(C(=O)c1cscn1)C2] |
| Example 51 | N-{[4-hydroxy-2-oxo-1-(3-pyridin-4-ylbenzyl)-6-(1,3-thiazol-3-ium-4-ylcarbonyl)-2,5,6,7-tetrahydro-1H-pyrrolo[3,4-b]pyridin-3-yl]carbonyl}glycine trifluoroacetate | 531.9 2.13 | 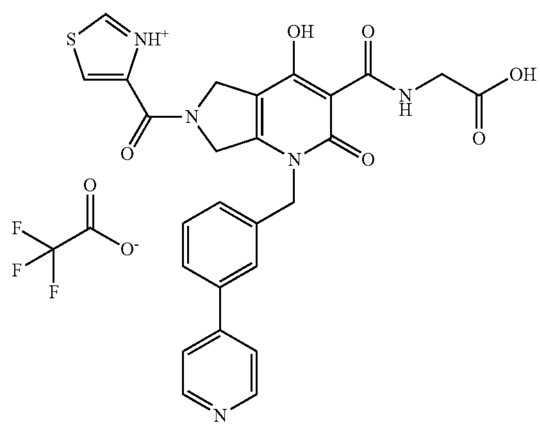 [SMILES: O=C([O-])C(F)(F)F ; O=C(O)CNC(=O)c1c(O)c2c(n(Cc3cccc(-c4ccncc4)c3)c1=O)CN(C(=O)c1csc[nH+]1)C2] |
| Example 52 | N-{[4-hydroxy-2-oxo-1-(3-pyridin-3-ylbenzyl)-6-(1,3-thiazol-3-ium-4-ylcarbonyl)-2,5,6,7-tetrahydro-1H-pyrrolo[3,4-b]pyridin-3-yl]carbonyl}glycine trifluoroacetate | 531.9 2.17 | 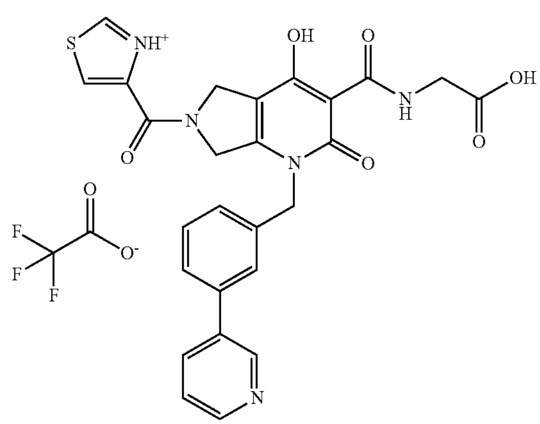 [SMILES: O=C([O-])C(F)(F)F ; O=C(O)CNC(=O)c1c(O)c2c(n(Cc3cccc(-c4cccnc4)c3)c1=O)CN(C(=O)c1csc[nH+]1)C2] |

TABLE 8-continued

| Example | Name | HPLC/MS m/z (M + 1) R$_t$ (min) | Structure |
|---|---|---|---|
| Example 53 | N-{[1-[3-(6-fluoropyridin-3-yl)benzyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine | 549.8 2.87 | 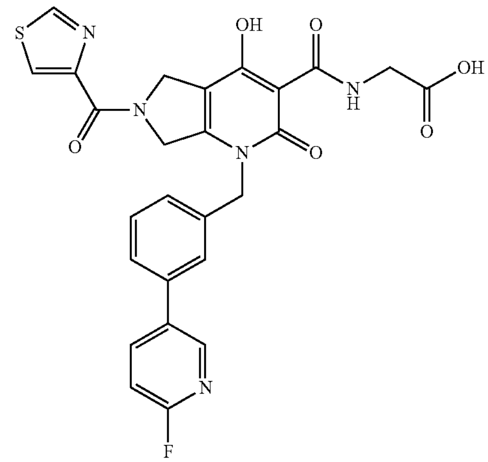 [SMILES: O=C(O)CNC(=O)c1c(O)c2c(n(Cc3cccc(-c4ccc(F)nc4)c3)c1=O)CN(C(=O)c1cscn1)C2] |

Example 54

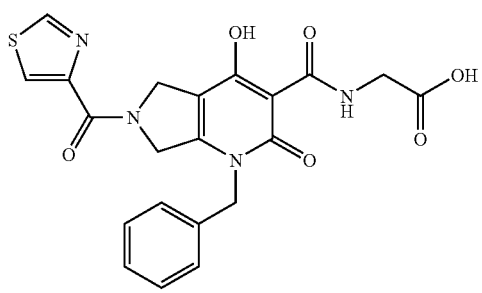

N-{[1-benzyl-4-hydroxy-2-oxo-6-(1,3-thiazol-4-ylcarbonyl)-2,5,6,7-tetrahydro-1H-pyrrolo[3,4-b]pyridin-3-yl]carbonyl}glycine (E54-1)

In a failed attempt to couple cyclohexyl boronic acid with tert-butyl N-{[1-(2-bromobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycinate (prepared in similar fashion to Intermediate 5), and using a similar procedure to that described in Example 49 Step A, the above side product, compound E54-1 obtained. HPLC/MS: 454.9 (M+1); R$_t$=2.67 min.

Example 55

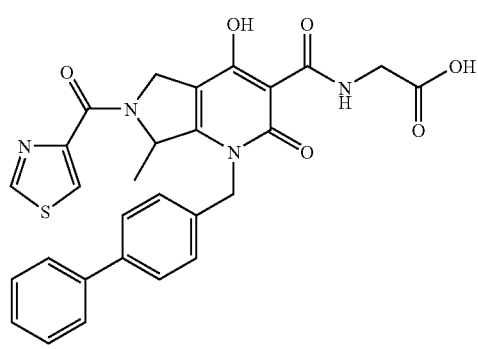

N-{[1-(biphenyl-4-ylmethyl)-4-hydroxy-7-methyl-2-oxo-6-(1,3-thiazol-4-ylcarbonyl)-2,5,6,7-tetrahydro-1H-pyrrolo[3,4-b]pyridin-3-yl]carbonyl}glycine (E55-1)

Step A: 1,3-Thiazole-4-carbonyl chloride (E55-a)

To 1,3-thiazole-4-carboxylic acid (0.423 g, 3.28 mmol) in CH$_2$Cl$_2$ (10 mL) was added oxalyl chloride (0.34 mL, 3.93 mL) and DMF (5 drops). The reaction was warmed momentarily to about 30-35° C. and then stirred at rt for 2 h. The reaction was concentrated to afford the product.

Step B: tert-Butyl N-{[1-(4-bromobenzyl)-4-hydroxy-7-methyl-2-oxo-6-(1,3-thiazol-4-ylcarbonyl)-2,5,6,7-tetrahydro-1H-pyrrolo[3,4-b]pyridin-3-yl]carbonyl}glycinate (E55-b)

To tert-butyl N-{[1-(4-bromobenzyl)-4-hydroxy-7-methyl-2-oxo-2,5,6,7-tetrahydro-1H-pyrrolo[3,4-b]pyridin-3-yl]carbonyl}glycinate (1.344 g, 2.73 mmol, prepared in similar fashion to Intermediate 6 utilizing the appropriate starting materials) was added the product of Step A (0.403 g, 2.73 mmol) and NEt$_3$ (0.38 mL, 2.73 mL). The reaction stirred at rt for about 17 h and was then diluted with EtOAc and washed with aq Na$_2$CO$_3$ (2 M) and brine. The concentrated residue was purified by flash chromatography on silica gel gradient eluted with 0-65% EtOAc/hexane to afford the product.

Step C: tert-butyl N-{[1-(biphenyl-4-ylmethyl)-4-hydroxy-7-methyl-2-oxo-6-(1,3-thiazol-4-ylcarbonyl)-2,5,6,7-tetrahydro-1H-pyrrolo[3,4-b]pyridin-3-yl]carbonyl}glycinate (E55-c)

E55-c was prepared using a procedure similar to that described in Example 49 Step A. Both enantiomers were separated on an IA chiral column eluting with 55% IPA/heptane.

Step D: N-{[1-(biphenyl-4-ylmethyl)-4-hydroxy-7-methyl-2-oxo-6-(1,3-thiazol-4-ylcarbonyl)-2,5,6,7-tetrahydro-1H-pyrrolo[3,4-b]pyridin-3-yl]carbonyl}glycine (E55-b)

Both the enantiomers isolated in step C were independently treated to conditions similar to that of Example 7 to afford the title compound, E55-1. HPLC/MS: 544.9 (M+1); $R_t$=3.20 min.

Example 56

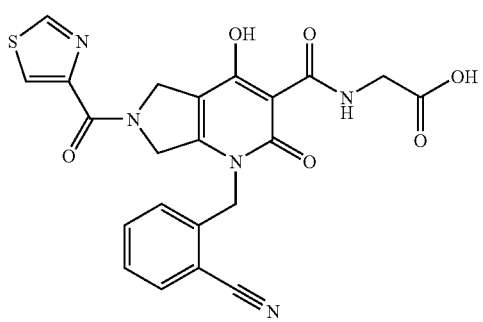

E56-1

N-{[1-(2-cyanobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine (E56-1)

Step A: tert-butyl N-{[1-(2-cyanobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycinate (E56-a)

tert-Butyl N-{[1-(2-bromobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycinate (0.2 g, 0.34 mmol, prepared in similar fashion to Intermediate 5) was dissolved in DMF (4 mL) and water (0.04 mL). $Zn(CN)_2$ (40 mg, 0.34 mmol), dppf (24.8 mg, 0.045 mmol) and $Pd_2(dba)_3$ (17 mg, 0.019 mmol) were added and the flask was evacuated and backfilled with nitrogen 3 times. The mixture was heated at 110° C. overnight. The reaction was cooled and partitioned between EtOAc and 2 M HCl, dried ($Na_2SO_4$), filtered and concentrated. The residue was purified by flash chromatography on silica gel gradient eluted with 0-100% EtOAc in hexane affording the product.

Step B: N-{[1-(2-cyanobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine The product of Step A (20 mg, 0.037 mmol) was dissolved in DCM (1.5 mL) and TFA (0.5 mL, 6.5 mmol) was added. The reaction was stirred at ambient temperature overnight. The reaction was concentrated and the residue was purified on a C-18 reverse phase chromatography column eluted with 0-100% MeCN in water. The desired fractions were concentrated affording the title compound. 480.0 (M+1); $R_t$=2.53 min.

Biological Assays

The exemplified compounds, Examples 1 through 56, of the present invention, have been found to inhibit the interaction between PHD2 and a HIF peptide and exhibit $IC_{50}$ values ranging between 1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 96-well plate was added 1 µL of test compound in DMSO and 20 µl of assay buffer (50 mM Tris pH 7.4/0.01% Tween-20/0.1 mg/ml bovine serum albumin/10 µM ferrous sulfate/1 mM sodium ascorbate/20 µg/ml catalase) containing 0.15 µg/ml FLAG-tagged full length PHD2 expressed in and purified from baculovirus-infected Sf9 cells. After a 30 min preincubation at room temperature, the enzymatic reactions were initiated by the addition of 4 µL of substrates (final concentrations of 0.2 µM 2-oxoglutarate and 0.5 µM HIF-1α peptide biotinyl-DLDLEMLAPYIPMD-DDFQL). After 2 hr at room temperature, the reactions were terminated and signals were developed by the addition of a 25 µL quench/detection mix to a final concentration of 1 mM ortho-phenanthroline, 0.1 mM EDTA, 0.5 nM anti-(His)$_6$ LANCE reagent (Perkin-Elmer Life Sciences), 100 nM AF647-labeled streptavidin (Invitrogen), and 2 µg/ml (His)$_6$-VHL complex (S. Tan(2001) Protein Expr. Purif 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

Table 9 lists the PHD2 binding activity expressed as $IC_{50}$ (nM), for the compounds of the present invention disclosed in Examples 1 through 56.

TABLE 9

| PHD2 Binding Activity | |
|---|---|
| Example | PHD2 Activity |
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |

TABLE 9-continued

PHD2 Binding Activity

| Example | PHD2 Activity |
|---|---|
| 27 | + |
| 28 | + |
| 29 | + |
| 30 | + |
| 31 | + |
| 32 | + |
| 33 | ++ |
| 34 | + |
| 35 | + |
| 36 | + |
| 37 | + |
| 38 | + |
| 39 | + |
| 40 | ++ |
| 41 | ++ |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | Enantiomer 1 + |
| 55 | Enantiomer 2 ++ |
| 56 | + |

+ = ≦10 IC$_{50}$ (nM)
++ = >10 to ≦100 IC$_{50}$ (nM)

What is claimed is:

1. A compound of formula I and pharmaceutically acceptable salts and solvates thereof

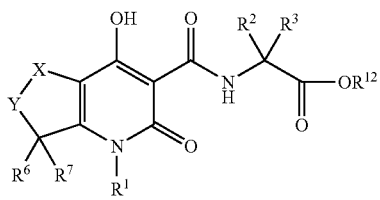

I wherein
one of X, or Y, is NR$^8$ and the other moiety is —CR$^4$R$^5$;
R$^{12}$ is selected from hydrogen, C$_{1-6}$ alkyl, optionally substituted with a hydroxy, —SH, —NH$_2$ or —CO$_2$H, and C$_{3-6}$ cycloalkyl optionally substituted with a hydroxy, —SH, —NH$_2$ or —CO$_2$H;
n is 1, or 2;
R$^1$ is selected from
—C$_{1-10}$ alkyl,
—C$_{2-10}$ alkenyl,
—C$_{5-10}$ cycloalkenyl,
—C$_{2-10}$ alkynyl,
—C$_{0-10}$ alkylaryl,
—C$_{0-10}$ alkylheterocyclyl;
—C$_{0-10}$ alkylC$_{3-10}$cycloalkyl,
—C$_{0-10}$ alkylC$_{3-10}$heterocycloalkyl, and
perfluoroC$_{1-6}$alkyl;

wherein in R$^1$ said alkyl, alkenyl, alkynyl, cycloalkenyl, aryl, heterocycloalkyl, heterocyclyl, and cycloalkyl are each optionally substituted with one or more R$^9$ substituents;

R$^2$ and R$^3$ are independently selected from hydrogen, phenyl, heterocyclyl, and —C$_{1-10}$ alkyl, wherein C$_{1-10}$ alkyl is unsubstituted or substituted with one or more fluorine atoms, and phenyl is unsubstituted or substituted with or more substituents selected from fluoro, chloro, hydroxyl, C$_{1-10}$ alkyl, and —OC$_{1-10}$ alkyl;

R$^8$ is selected from —C$_1$-C$_{10}$ alkyl, —C$_{2-10}$ alkenyl, —(C$_{0-10}$ alkyl)C$_{3-10}$ cycloalkyl, —(C$_{0-10}$ alkyl) C$_{3-10}$ heterocycloalkyl, —(C$_{0-10}$ alkyl)aryl, —(C$_{0-10}$ alkyl) heterocyclyl, —(C$_{0-10}$ alkyl)C$_{5-10}$ cycloalkenyl, C$_{1-6}$ alkoxy, aryloxy, heterocyclyloxy, —CO$_2$R$^a$, —CONR$^b$R$^c$, —R$^a$C(=N)NR$^b$R$^c$, —S(O)$_2$NR$^b$, and —S(O)$_n$R$^d$, wherein said aryl, heterocyclyl, alkoxy, aryloxy, heterocyclyloxy are optionally substituted by one or more substituents R$^{10}$;

R$^4$, R$^5$, R$^6$, and R$^7$ are independently selected from hydrogen, cyano, oxo, —C$_1$-C$_{10}$ alkyl, —C$_{2-10}$ alkenyl, —C$_{3-10}$ cycloalkyl, —(C$_{0-10}$ alkyl)aryl, (C$_{0-10}$ alkyl)heterocyclyl, —C$_{5-10}$ cycloalkenyl, —C$_{2-10}$ alkynyl, —SO$_n$(C$_{1-10}$ alkyl) and —SO$_n$aryl wherein said alkyl, alkenyl, alkynyl, cycloalkyl, cycloalkenyl, aryl, and heterocyclyl are optionally substituted by one or more substituents R$^9$, and optionally one set of substituents, R$^4$ and R$^5$, or R$^6$ and R$^7$, are linked together to form a ring of 5 to 8 atoms optionally substituted with one or more substituents R$^9$;

where said ring is partially or fully unsaturated having 0, 1 or 2 heteroatoms independently selected from —NR$^6$—, —O— and —S(O)$_n$—;

R$^9$ is selected from halogen, hydroxy, oxo, cyano, aryl, heterocyclyl, —C$_{1-6}$ alkyl, —C$_{1-6}$ alkoxy, aryloxy, heterocyclyloxy, —CO$_2$R$^a$, —NR$^b$R$^c$, —CONR$^b$R$^c$, —OCO$_2$R$^a$, —OCONR$^b$R$^c$, —NR$^d$CO$_2$R$^a$, —NR$^d$CONR$^b$R$^c$, —SC$_{0-6}$ alkyl and —S(O)$_n$R$^d$, wherein said aryl, heterocyclyl, alkoxy, aryloxy, heterocyclyloxy are optionally substituted by one or more substituents R$^{10}$;

R$^{10}$ is selected from hydroxy, aryl, heterocyclyl, halogen, oxo, —C$_{1-6}$ alkyl, C$_{1-6}$ alkoxy, halogen, CO$_2$H, cyano, O(C=O)$_{0-1}$C$_{1-6}$ alkyl, NO$_2$, trifluoromethoxy, trifluoroethoxy, —O$_{(0-1)}$(C$_{1-10}$)perfluoroalkyl, C$_{0-10}$ alkylaminocarbonylamino, C$_{0-10}$ alkyloxycarbonylaminoC$_{0-10}$ alkyl, C$_{0-10}$ alkylcarbonylaminoC$_{0-10}$ alkyl, C$_{0-10}$ alkylaminosulfonylaminoC$_{0-10}$ alkyl, C$_{0-10}$ alkylsulfonylaminoC$_{0-10}$ alkyl, C$_{0-10}$ alkylsulfonyl, C$_{0-10}$ alkylaminosulfonyl, C$_{0-10}$ alkylaminocarbonyl, —(C=O)N (C$_{0-6}$ alkyl)$_2$, —S(C$_{0-6}$ alkyl), and NH$_2$;

R$^a$ is chosen from hydrogen; —C$_{1-10}$ alkyl; —(C$_{1-6}$ alkyl) C$_{3-8}$ cycloalkyl; and —(C$_{1-6}$ alkyl)phenyl; and R$^b$, R$^c$, and R$^d$ are each independently chosen from hydrogen, —C$_{1-10}$ alkyl, —C$_{3-10}$ cycloalkyl, aryl, and heterocyclyl, wherein said alkyl, cycloalkyl, aryl and heterocyclyl are optionally substituted by one or more subtstituents R$^{10}$.

2. A compound of claim 1 wherein X is —NR$^8$ and Y is CR$^4$R$^5$.

3. A compound of claim 1 wherein Y is —NR$^8$ and X is CR$^4$R$^5$.

4. A compound of claim 1 wherein R$^1$ is selected from —C$_{0-10}$ alkylaryl, and —C$_{0-10}$ alkylheterocyclyl.

5. A compound of claim 4, wherein $C_{0-10}$ alkylaryl is —$C_{1-3}$ alkylaryl and the aryl moiety is selected from phenyl, naphthyl, tetrahydro-naphthyl, indanyl, 2,3-dihydro-1H-indenyl, and biphenyl phenyl.

6. A compound of claim 4 wherein $R^8$ is selected from —$C_1$-$C_{10}$ alkyl, —$C_{2-10}$ alkenyl, —($C_{0-10}$ alkyl)$C_{3-10}$ cycloalkyl, —($C_{0-10}$ alkyl) $C_{3-10}$ heterocycloalkyl, —($C_{0-10}$ alkyl)aryl, —($C_{0-10}$ alkyl)heterocyclyl, $C_{1-6}$ alkoxy, aryloxy, heterocyclyloxy, —S(O)$_2$NR$^b$, and —S(O)$_n$R$^d$, wherein said aryl, heterocyclyl, alkoxy, aryloxy, heterocyclyloxy are optionally substituted by one or more substituents $R^{10}$.

7. A compound of claim 6, wherein $R^8$ is selected from —$C_1$-$C_{10}$ alkyl, —$C_{2-10}$ alkenyl, —($C_{1-10}$ alkyl)$C_{3-10}$ cycloalkyl, —($C_{1-10}$ alkyl)$C_{3-10}$ heterocycloalkyl, —($C_{1-10}$ alkyl)aryl, —($C_{1-10}$ alkyl)heterocyclyl, $C_{1-6}$ alkoxy, aryloxy, heterocyclyloxy, —S(O)$_2$NR$^b$, and —S(O)$_n$R$^d$, wherein said aryl, heterocyclyl, alkoxy, aryloxy, heterocyclyloxy are optionally substituted by one or more substituents $R^{10}$.

8. A compound of claim 4 wherein $R^1$ is —$C_{0-10}$ alkylheterocyclyl.

9. A compound of claim 8, wherein in the —$C_{0-10}$ alkylheterocyclyl of $R^1$, the heterocyclyl moiety is selected from azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

10. A compound of claim 9, wherein in the —$C_{0-10}$ alkylheterocyclyl of $R^1$, wherein —$C_{1-3}$alkylheterocyclyl is selected from pyrimidinylphenyl, pyridinylphenyl, pyridinyl, thiazolyl, oxadiazolyl, benzothiazolyl, oxazolyl, quinolyl, benzothienyl, pyrazolyl, pyrazinyl, and pyridinyl.

11. A compound selected from:
N-({4-hydroxy-2-oxo-6-pent-4-enoyl-1-[4-(trifluoromethyl)benzyl]-2,5,6,7-tetrahydro-1H-pyrrolo[3,4-b]pyridin-3-yl}carbonyl)glycine;
N-{[1-(biphenyl-4-ylmethyl)-4-hydroxy-2-oxo-6-pent-4-enoyl-2,5,6,7-tetrahydro-1H-pyrrolo[3,4-b]pyridin-3-yl]carbonyl}glycine;
N-{[1-(1,3-benzothiazol-2-ylmethyl)-4-hydroxy-2-oxo-6-pent-4-enoyl-2,5,6,7-tetrahydro-1H-pyrrolo[3,4-b]pyridin-3-yl]carbonyl}glycine;
N-{[1-(3-bromobenzyl)-4-hydroxy-2-oxo-6-pent-4-enoyl-2,5,6,7-tetrahydro-1H-pyrrolo[3,4-b]pyridin-3-yl]carbonyl}glycine;
N-{[1-(4-bromobenzyl)-4-hydroxy-7-methyl-2-oxo-6-pent-4-enoyl-2,5,6,7-tetrahydro-1H-pyrrolo[3,4-b]pyridin-3-yl]carbonyl}glycine;
N-{[1-(4-bromobenzyl)-4-hydroxy-5-methyl-2-oxo-6-pent-4-enoyl-2,5,6,7-tetrahydro-1H-pyrrolo[3,4-b]pyridin-3-yl]carbonyl}glycine;
N-({4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate;
N-({6-(3-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({6-acetyl-4-hydroxy-2-oxo-1-[4-(trifluoromethyl)benzyl]-2,5,6,7-tetrahydro-1H-pyrrolo[3,4-b]pridin-3-yl}carbonyl)glycine;
N-({4-hydroxy-6-(methylsulfonyl)-2-oxo-1-[4-(trifluoromethyl)benzyl]-2,5,6,7-tetrahydro-1H-pyrrolo[3,4-b]pyridin-3-yl}carbonyl)glycine;
N-({4-hydroxy-6-(morpholin-4-ylcarbonyl)-2-oxo-1-[4-(trifluoromethyl)benzyl]-2,5,6,7-tetrahydro-1H-pyrrolo[3,4-b]pyridin-3-yl}carbonyl)glycine;
N-({6-[(dimethylamino)sulfonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({6-(cyclopropylcarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({4-hydroxy-6-(methoxyacetyl)-2-oxo-1-[4-(trifluoromethyl)benzyl]-2,5,6,7-tetrahydro-1H-pyrrolo[3,4-b]pyridin-3-yl}carbonyl)glycine;
N-({6-(2,2-dimethylpropanoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({6-(ethoxycarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({4-hydroxy-2-oxo-6-(pyrrolidin-1-ylcarbonyl)-1-[4-(trifluoromethyl)benzyl]-2,5,6,7-tetrahydro-1H-pyrrolo[3,4-b]pyridin-3-yl}carbonyl)glycine;
N-({6-(2-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({4-hydroxy-2-oxo-6-(phenylsulfonyl)-1-[4-(trifluoromethyl)benzyl]-2,5,6,7-tetrahydro-1H-pyrrolo[3,4-b]pyridin-3-yl}carbonyl)glycine;
N-({6-(cyclopentylcarbonyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({6-(4-chlorobenzoyl)-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-{[1-(biphenyl-4-ylmethyl)-6-(ethoxycarbonyl)-4-hydroxy-2-oxo-2,5,6,7-tetrahydro-1H-pyrrolo[3,4-b]pyridin-3-yl]carbonyl}glycine;
N-({6-[(1,3-dimethyl-1H-pyrazol-5-yl)carbonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine;
N-({4-hydroxy-2-oxo-6-(pyrazolo[1,5-a]primidin-2-ylcarbonyl)-1-[4-(trifluoromethyl)benzyl]-2,5,6,7-tetrahydro-1H-pyrrolo[3,4-b]pyridin-3-yl}carbonyl)glycine;
N-({4-hydroxy-2-oxo-6-(pyridin-3-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-6-[(6-methylpyridin-3-yl)carbonyl]-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-6-(1-methyl-L-prolyl)-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(5-oxo-L-prolyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,3-thiazol-4-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,3-thiazol-5-ylcarbonyl)-1-[4-(trifluoromethyl)benzyl]-2,5,6,7-tetrahydro-1H-pyrrolo[3,4-b]pyridin-3-yl}carbonyl)glycine;

N-({6-[(1,5-dimethyl-1H-pyrazol-2-ium-3-yl)carbonyl]-4-hydroxy-2-oxo-1-[4-(trifluoromethyl)benzyl]-2,5,6,7-tetrahydro-1H-pyrrolo[3,4-b]pyridin-3-yl}carbonyl)glycine chloride;

N-({4-hydroxy-6-{[(2S)-1-methylpyrrolidinium-2-yl]carbonyl}-2-oxo-1-[4-(trifluoromethyl)benzyl]-2,5,6,7-tetrahydro-1H-pyrrolo[3,4-b]pyridin-3-yl}carbonyl)glycine trifluoroacetate;

N-({4-hydroxy-6-(isoxazol-5-ylcarbonyl)-2-oxo-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,3-thiazol-2-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-2-oxo-6-(1,2,3-thiadiazol-4-ylcarbonyl)-1-[4-(trifluoromethyl)benzyl]-2,5,6,7-tetrahydro-1H-pyrrolo[3,4-b]pyridin-3-yl}carbonyl)glycine;

N-({4-hydroxy-6-[(6-methylpyridinium-3-yl)carbonyl]-2-oxo-1-[4-(trifluoromethyl)benzyl]-2,5,6,7-tetrahydro-1H-pyrrolo[3,4-b]pyridin-3-yl}carbonyl)glycine trifluoroacetate;

N-({4-hydroxy-6-(1,3-oxazol-4-ylcarbonyl)-2-oxo-1-[4-(trifluoromethyl)benzyl]-2,5,6,7-tetrahydro-1H-pyrrolo[3,4-b]pyridin-3-yl}carbonyl)glycine;

N-{[1-(biphenyl-4-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-({6-(4-chlorobenzyl)-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate;

N-({6-(3-chlorobenzyl)-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine chloride;

N-({6-ethyl-4-hydroxy-2-oxo-1-[4-(trifluoromethyl)benzyl]-2,5,6,7-tetrahydro-1H-pyrrolo[3,4-b]pyridin-6-ium-3-yl}carbonyl)glycine trifluoroacetate;

N-({6-(3-cyanopyridinium-2-yl)-4-hydroxy-2-oxo-1-[4-(trifluoromethyl)benzyl]-2,5,6,7-tetrahydro-1H-pyrrolo[3,4-b]pyridin-3-yl}carbonyl)glycine trifluoroacetate;

N-{[1-(biphenyl-3-ylmethyl)-4-hydroxy-2-oxo-6-pent-4-enoyl-2,5,6,7-tetrahydro-1H-pyrrolo[3,4-b]pyridin-3-yl]carbonyl}glycine;

N-{[1-(biphenyl-3-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-[(4'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pridin-3-yl]carbonyl}glycine;

N-{[4-hydroxy-2-oxo-1-(3-pyrimidin-5-ylbenzyl)-6-(1,3-thiazol-4-ylcarbonyl)-2,5,6,7-tetrahydro-1H-pyrrolo[3,4-b]pyridin-3-yl]carbonyl}glycine;

N-{[1-[(2'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(biphenyl-4-ylmethyl)-4-hydroxy-7-methyl-2-oxo-6-pent-4-enoyl-2,5,6,7-tetrahydro-1H-pyrrolo[3,4-b]pyridin-3-yl]carbonyl}glycine;

N-{[1-(biphenyl-2-ylmethyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-[(3'-chlorobiphenyl-3-yl)methyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[4-hydroxy-2-oxo-1-(3-pyridin-4-ylbenzyl)-6-(1,3-thiazol-3-ium-4-ylcarbonyl)-2,5,6,7-tetrahydro-1H-pyrrolo[3,4-b]pyridin-3-yl]carbonyl}glycine trifluoroacetate;

N-{[4-hydroxy-2-oxo-1-(3-pyridin-3-ylbenzyl)-6-(1,3-thiazol-3-ium-4-ylcarbonyl)-2,5,6,7-tetrahydro-1H-pyrrolo[3,4-b]pridin-3-yl]carbonyl}glycine trifluoroacetate;

N-{[1-[3-(6-fluoropyridin-3-yl)benzyl]-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(benzyl-4-hydroxy-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(biphenyl-4-ylmethyl)-4-hydroxy-7-methyl-2-oxo-6-(1,3-thiazol-4-ylcarbonyl)-2,5,6,7-tetrahydro-1H-pyrrolo[3,4-b]pyridin-3-yl]carbonyl}glycine;

N-{[1-(2-cyanobenzyl)-4-hydroxy-2-oxo-6-(1,3-thiazol-4-ylcarbonyl)-2,5,6,7-tetrahydro-1H-pyrrolo[3,4-b]pyridin-3-yl]carbonyl}glycine; and pharmaceutically acceptable salts and solvates thereof.

12. A pharmaceutical composition comprising a compound of claim 1 and pharmaceutically acceptable carrier.

13. A method of enhancing endogenous production of erythropoietin in a mammal which comprises administering to the mammal an amount of a compound of claim 1, or a pharmaceutically acceptable salt or solvate thereof, that is effective for enhancing endogenous production of erythropoietin.

14. A method for the treatment of anemia in a mammal which comprises administering to the mammal an effective amount of a compound of claim 1, or a pharmaceutically acceptable salt or solvate thereof.

* * * * *